(12) United States Patent
Meltola et al.

(10) Patent No.: US 9,518,186 B2
(45) Date of Patent: *Dec. 13, 2016

(54) LUMINESCENT LANTHANIDE CHELATES WITH ENHANCED EXCITATION PROPERTIES

(71) Applicant: Radiometer Turku Oy, Turku (FI)

(72) Inventors: Niko Meltola, Piispanristi (FI); Harri Takalo, Turku (FI); Henri Sund, Turku (FI)

(73) Assignee: Radiometer Turku OY, Turku (FI)

(*) Notice: Subject to any disclaimer, the term of this patent is extended or adjusted under 35 U.S.C. 154(b) by 320 days.

This patent is subject to a terminal disclaimer.

(21) Appl. No.: 13/723,505

(22) Filed: Dec. 21, 2012

(65) Prior Publication Data

US 2013/0183771 A1 Jul. 18, 2013
US 2014/0017807 A9 Jan. 16, 2014

Related U.S. Application Data

(60) Provisional application No. 61/578,977, filed on Dec. 22, 2011.

(30) Foreign Application Priority Data

Dec. 22, 2011 (DK) .................................. 2011 00996
Aug. 17, 2012 (WO) .................. PCT/EP2012/066082

(51) Int. Cl.
*C09B 57/00* (2006.01)
*G01N 33/58* (2006.01)
(Continued)

(52) U.S. Cl.
CPC ............ *C09B 57/00* (2013.01); *C07D 213/40* (2013.01); *C09B 57/10* (2013.01); *C09K 11/06* (2013.01);
(Continued)

(58) Field of Classification Search
None
See application file for complete search history.

(56) References Cited

U.S. PATENT DOCUMENTS 6,080,839 A 6/2000 Takalo et al.
6,402,986 B1 * 6/2002 Jones et al. .............. 252/301.16
(Continued)

FOREIGN PATENT DOCUMENTS

EP 0 967 205 A1 12/1999
EP 1 447 666 A2 8/2004
(Continued)

OTHER PUBLICATIONS

Takalo et al., "The influence of substituents on the luminescence properties of the Eu(III) and Tb(III) chelates of 4-(phenylethynyl)pyridine derivatives," J. Alloys and Compounds, 1995, vol. 225, issues 1-2, pp. 511-514.*

(Continued)

*Primary Examiner* — Galina Yakovleva
(74) *Attorney, Agent, or Firm* — Finnegan, Henderson, Farabow, Garrett & Dunner LLP

(57) ABSTRACT

The present application discloses a luminescent lanthanide chelate comprising one or more chromophoric moieties of the formula (I) or of the formula (III)

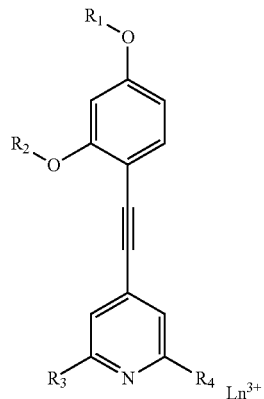

Formula (I)

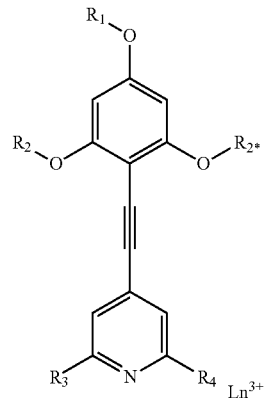

Formula (III)

wherein $R_1$, $R_2$ and $R_{2*}$ each independently are selected from carbon-containing substituents forming a C—O bond with the neighbouring oxygen atom, $R_3$ and $R_4$ each represent a bond between the chromophoric moiety and other moieties of the chelate, and $Ln^{3+}$ is a lanthanide ion, as well as the corresponding luminescence lanthanide chelating ligand. The application also discloses a detectable molecule comprising a biospecific binding reactant (such as an antibody) conjugated to the luminescent lanthanide chelate as well as a method of carrying out a biospecific binding assay, the use of such a detectable molecule in a specific bioaffinity based binding assay utilizing time-resolved fluorometric (Continued)

determination of a specific luminescence, and a solid support material conjugated with the luminescent lanthanide chelate.

11 Claims, 19 Drawing Sheets

(51) Int. Cl.
  *C09K 11/06* (2006.01)
  *C07D 213/04* (2006.01)
  *C09B 57/10* (2006.01)
  *C07D 213/40* (2006.01)
(52) U.S. Cl.
  CPC ....... *G01N 33/582* (2013.01); *C09K 2211/182* (2013.01); *G01N 2458/40* (2013.01)

(56) References Cited

U.S. PATENT DOCUMENTS

| | | |
|---|---|---|
| 2005/0181393 A1 | 8/2005 | Hovinen et al. |
| 2013/0210165 A1* | 8/2013 | Meltola et al. ............... 436/501 |

FOREIGN PATENT DOCUMENTS

| | | |
|---|---|---|
| JP | 2014-529559 | 11/2014 |
| WO | WO 00/48990 | 8/2000 |
| WO | WO 00/48991 | 8/2000 |
| WO | WO 2006/026038 A1 | 3/2006 |
| WO | WO 2008/020113 A1 | 2/2008 |
| WO | WO 2010/006605 A2 | 1/2010 |
| WO | WO 2010/055207 A1 | 5/2010 |
| WO | WO 2013/011236 A1 | 1/2013 |
| WO | WO 2013/026790 | 2/2013 |

OTHER PUBLICATIONS

Latva et al., "Correlation between the lowest triplet state energy level of the ligand and lanthanide(III) luminescence quantum yield," J. Luminescence, 1997, vol. 75, issue 2, pp. 149-169.*

International Search Report and Written Opinion mailed Jun. 10, 2013 for International Patent Applicat No. PCT/EP2012/076618.

Hovinen, Jari et al., "Bioconjugation with Stable Luminescent Lanthanide (III) Chelates Comprising Pyridine Subunits", *Bioconjugate Chem.*, 2009, 20, pp. 404-421.

Knapton, Daniel et al., "Fluorescent Organometallic Sensors for the Detection of Chemical-Warfare-Agent Mimics", *Angew. Chem. Int. Ed.*, 2006, 45, pp. 5825-5829.

Takalo, Harri et al., "Synthesis of Dimethyl and Diethyl 4-(Phenylethynyl)-2,6-pyridinedicarboxylate", *Acta Chemica Scandinavica* B41, 1987, pp. 219-221.

Takalo, Harri et al., "71. Synthesis and Luminescence of Novel $Eu^{III}$ Complexing Agents and Labels with 4-(Phenylethynyl) pyridine Subunits", *Helvetica Chimica Acta*, vol. 79, 1996, pp. 789-802.

Von Lode, Piia et al., "A Europium Chelate for Quantitative Point-of-Care Immunoassays Using Direct Surface Measurement", *Anal. Chem.*, 2003, 75, pp. 3193-3201.

Petterson et al, "Multi-Assay Point-of-Care Platform: Highly Sensitive Time-Resolved Fluorometric Detection in Combination with a Universal 'All-In-One' Assay Format," *Point of Care*, 3: 225-232 (2003).

* cited by examiner

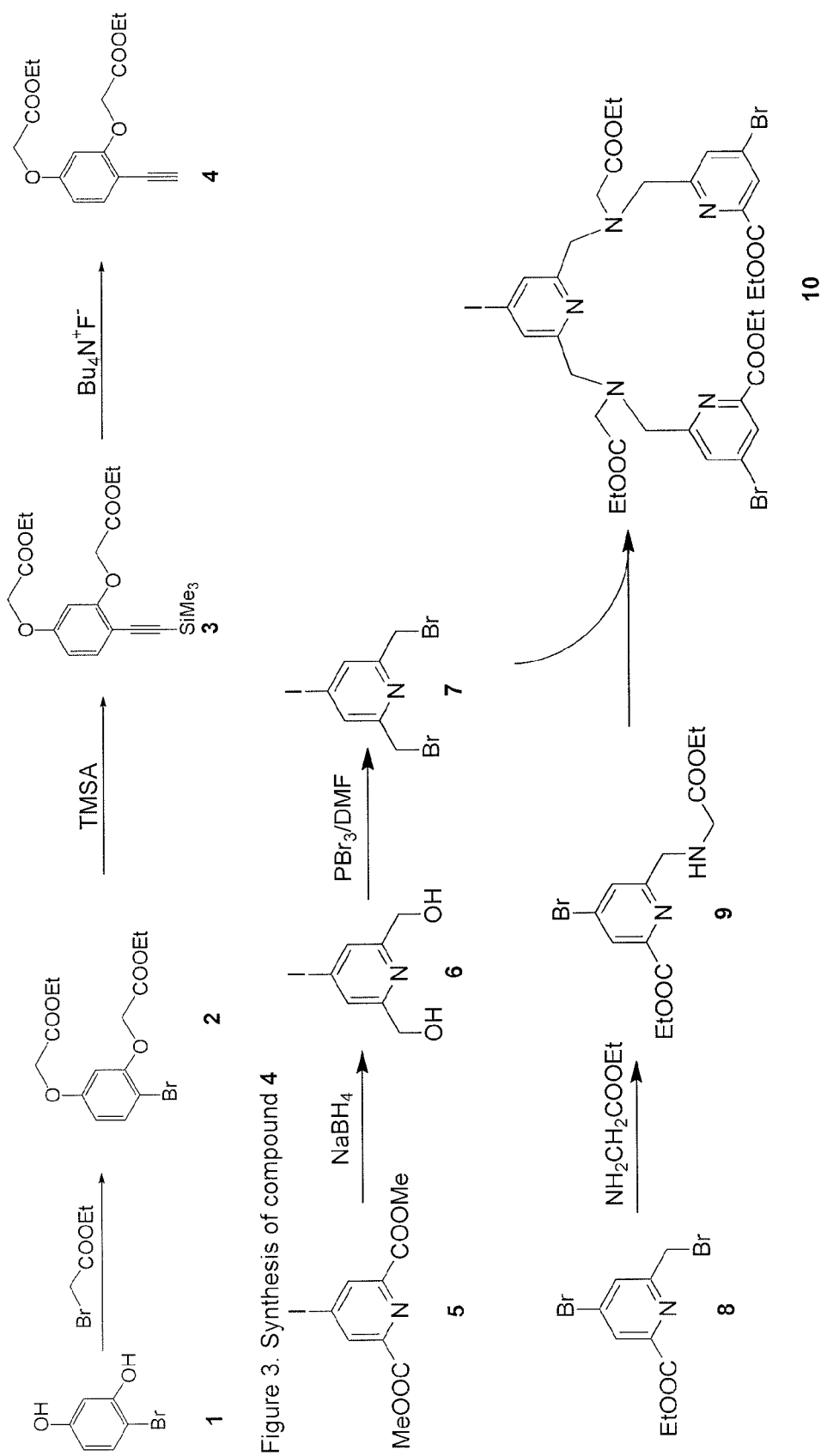
Figure 3. Synthesis of compound 4
Figure 4. Synthesis of compound 10

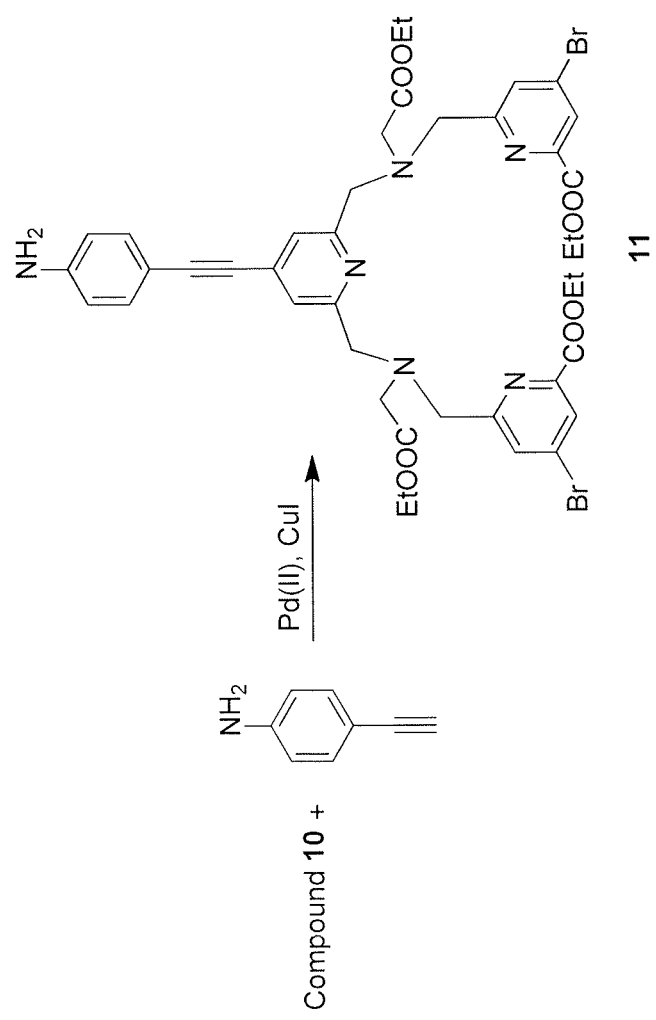
Figure 5. Synthesis of compound 11

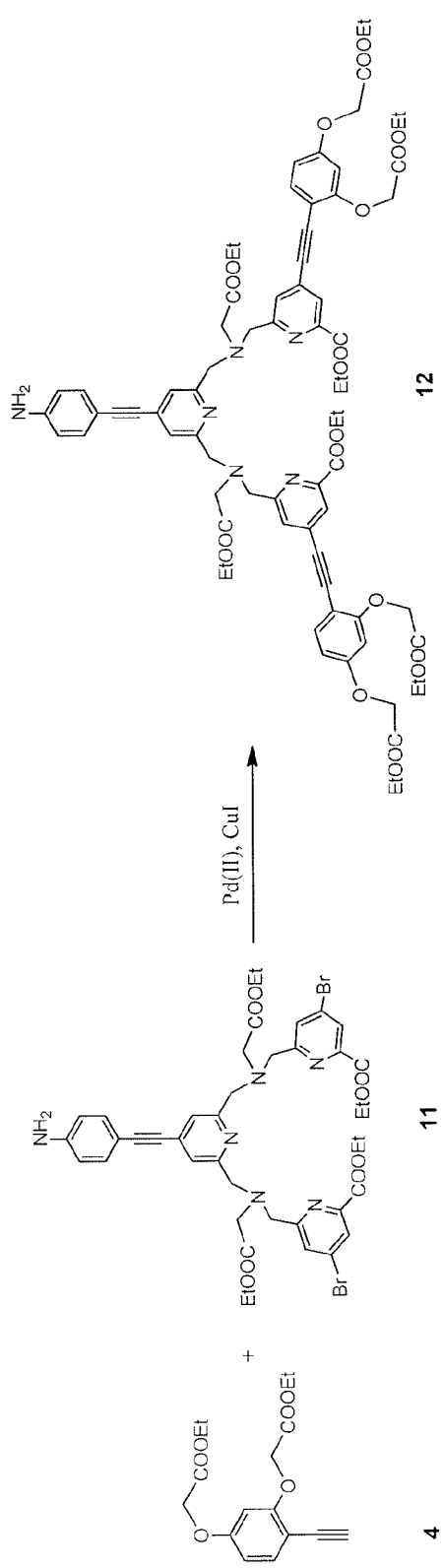
Figure 6. Synthesis of compound 12
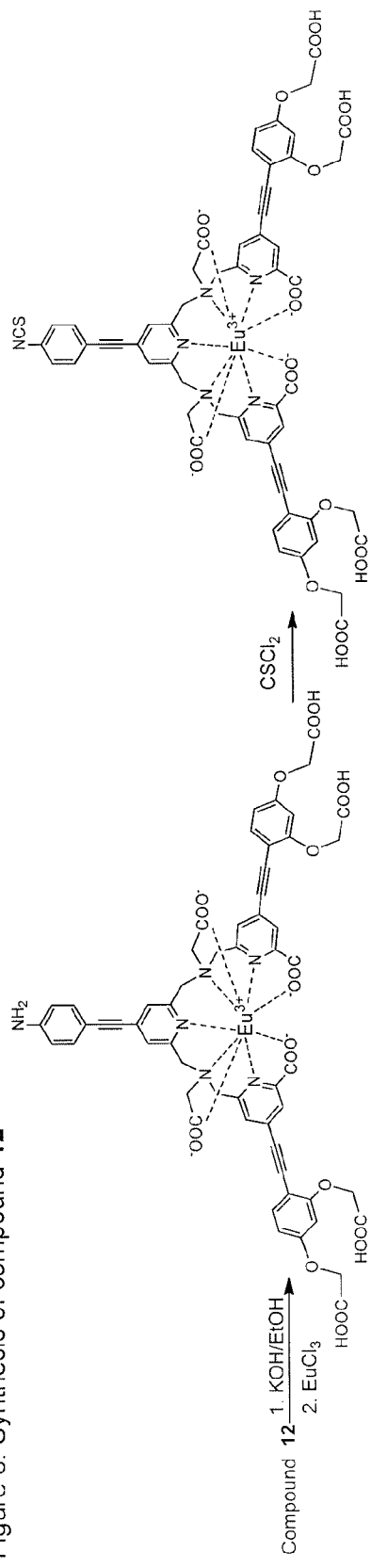
Figure 7. Synthesis of compound 14

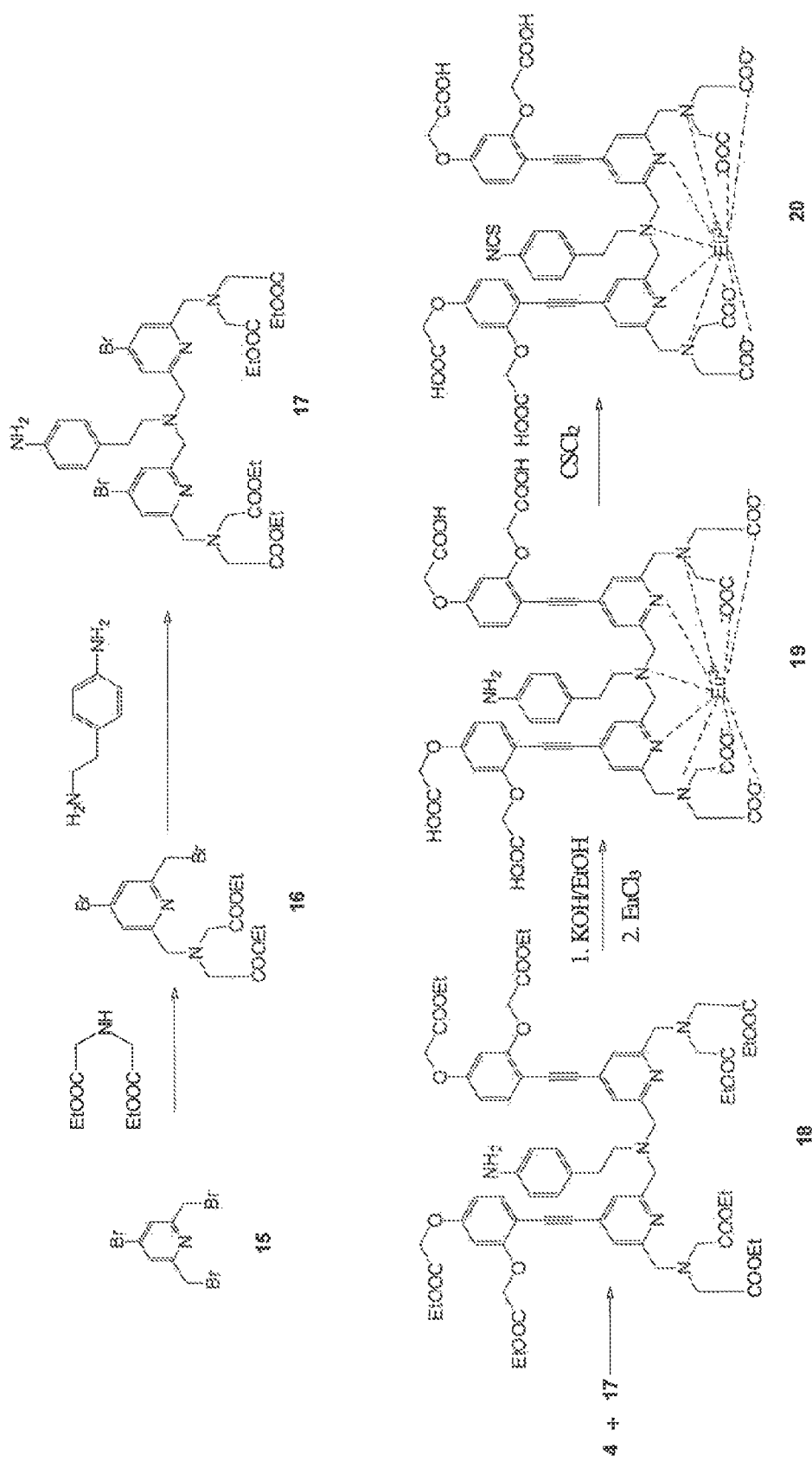
Figure 8. Synthesis of compound 20

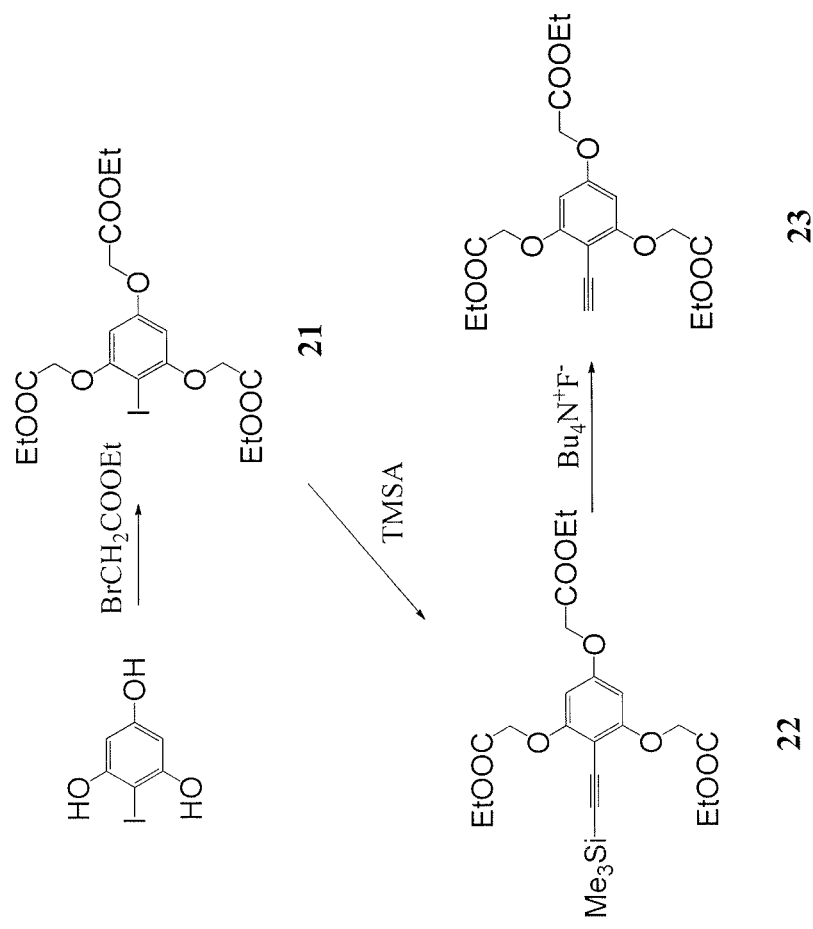
Figure 9. Synthesis of compound 23

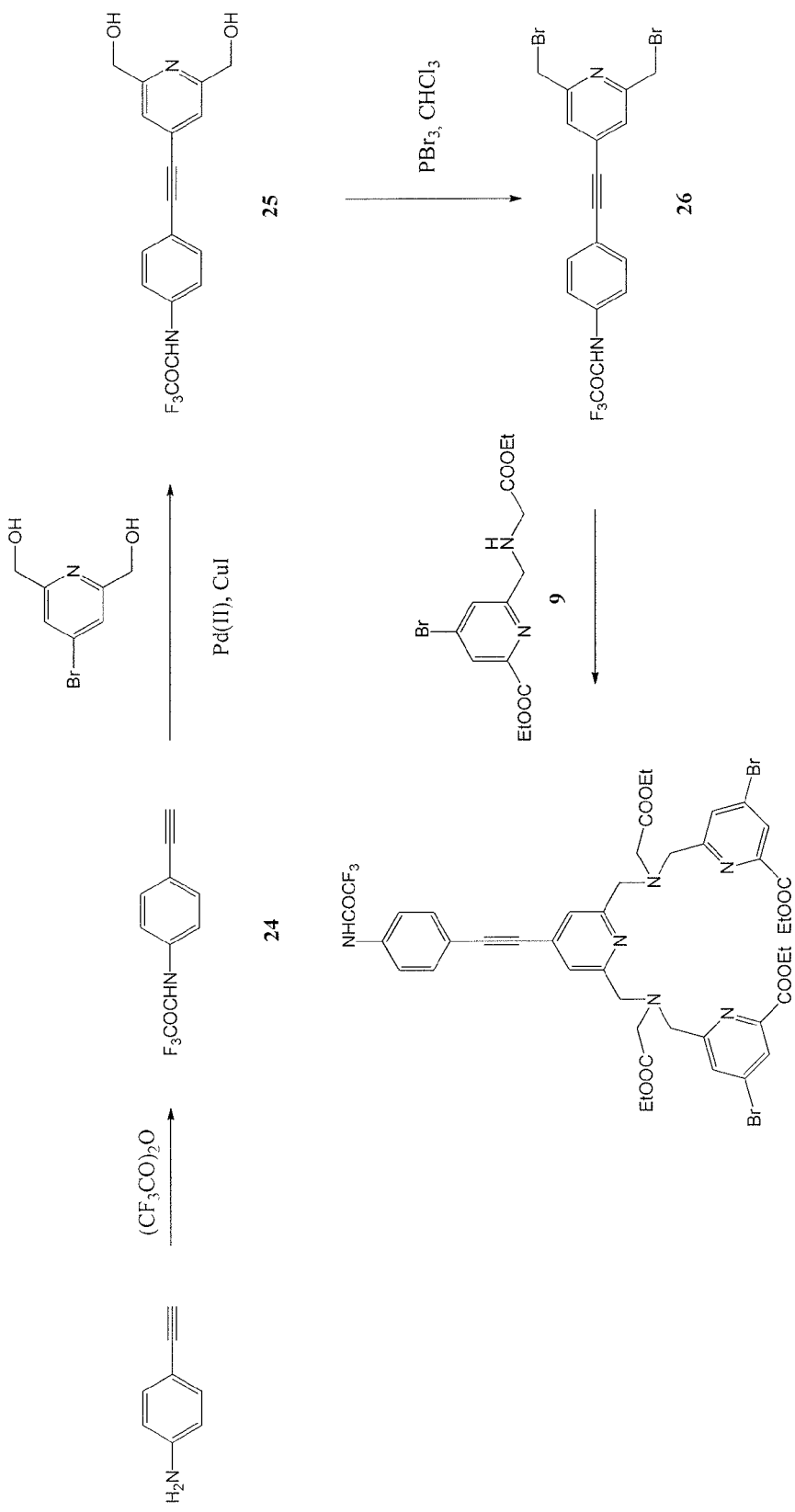
Figure 10. Synthesis of compound 27

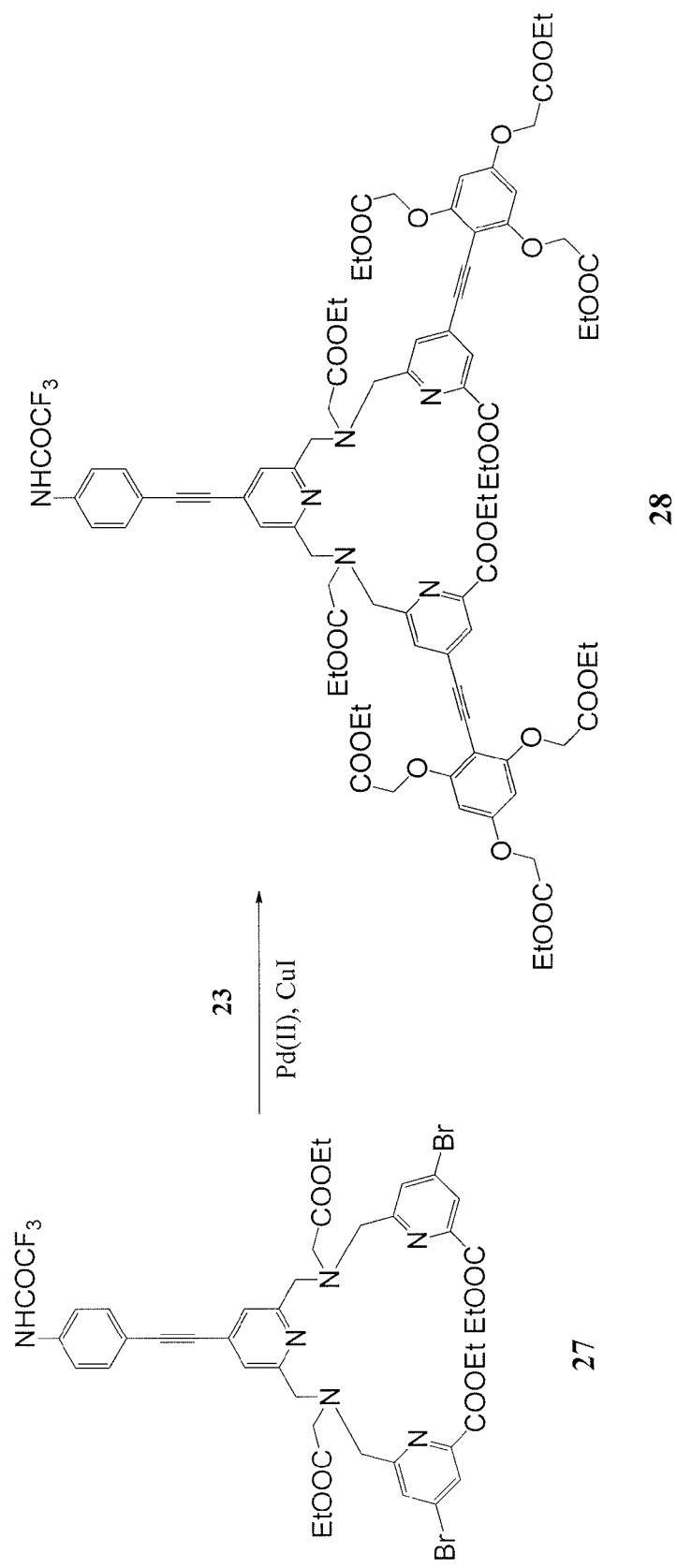
Figure 11. Synthesis of compound 28

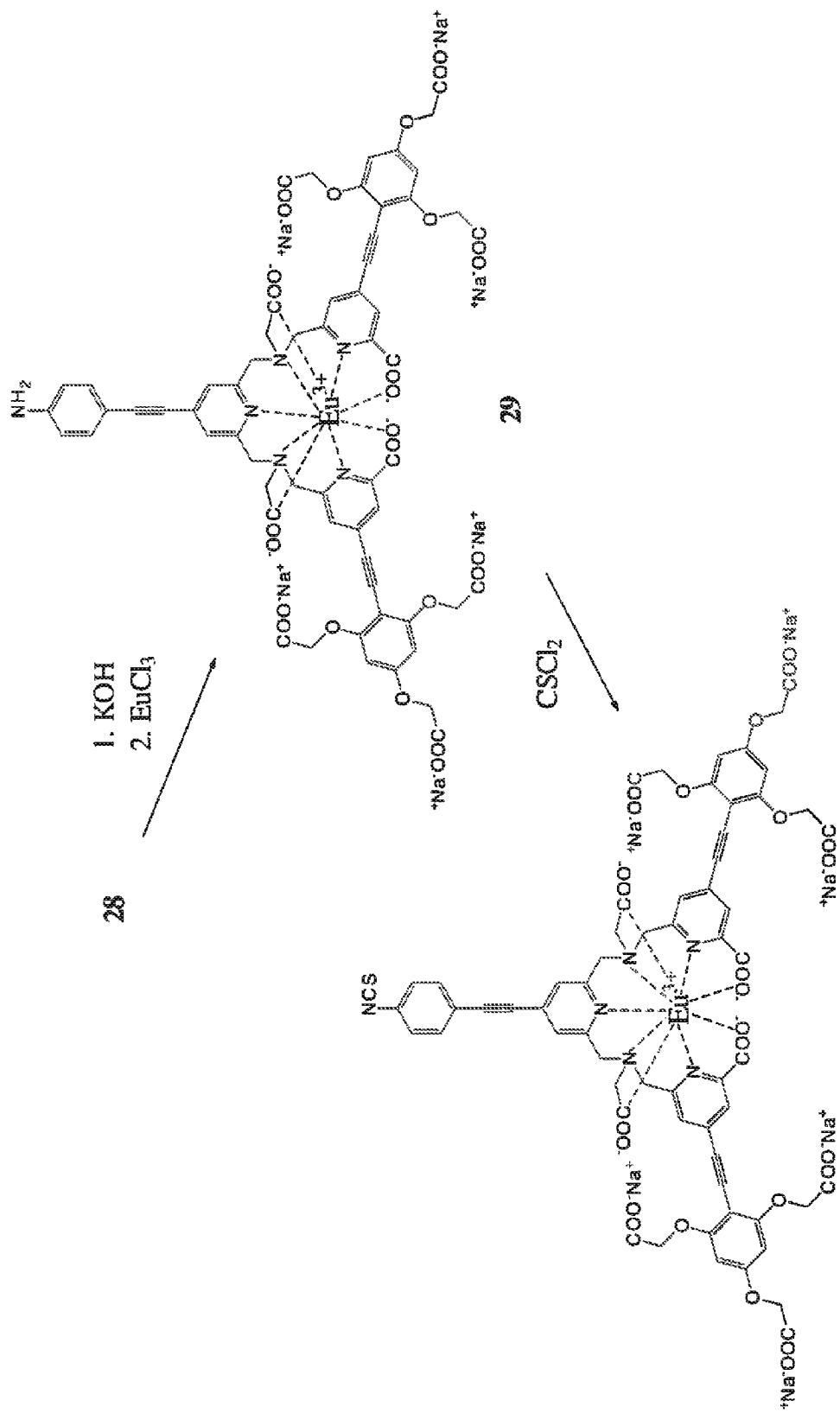
Figure 12. Synthesis of compound 30

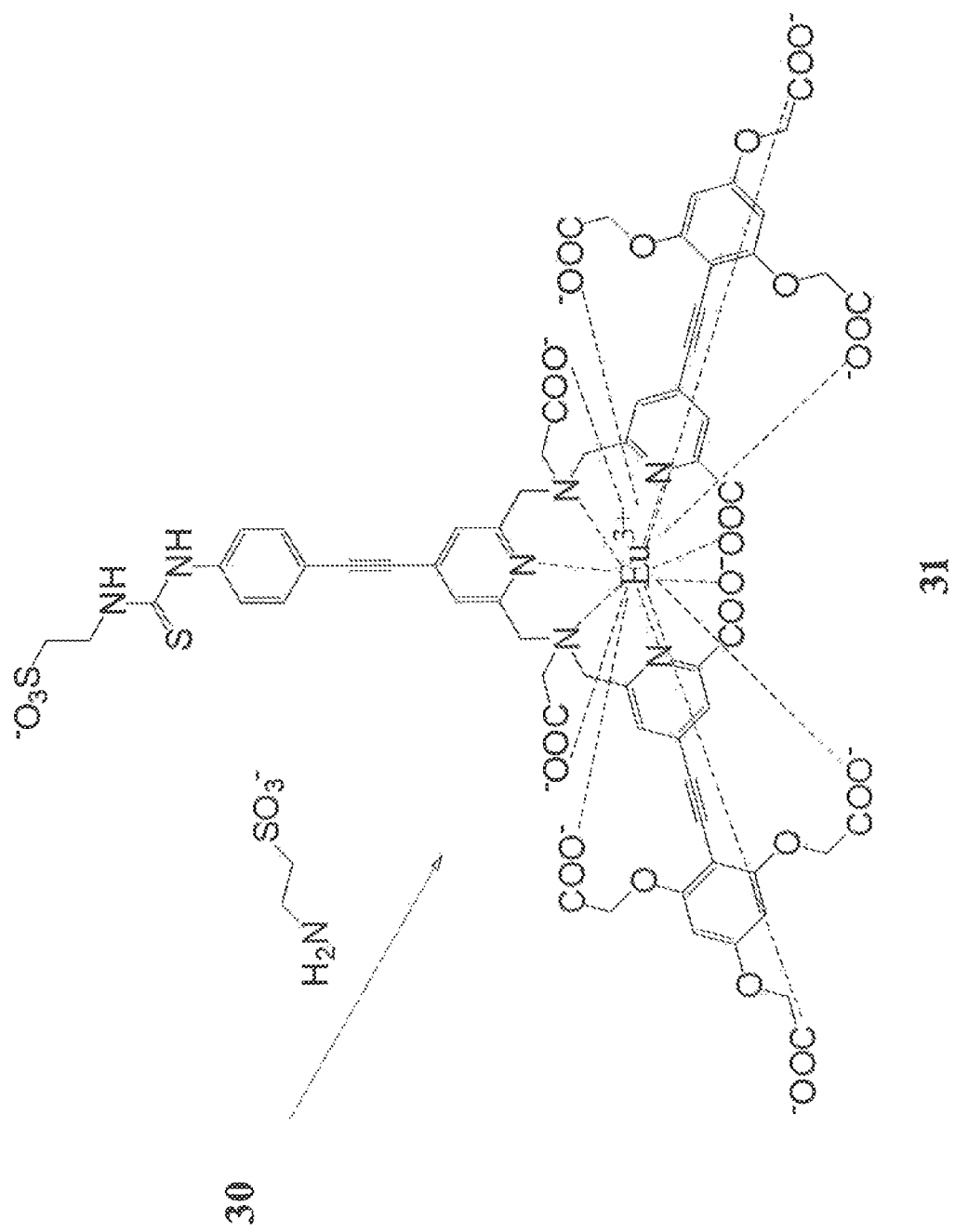
Figure 13. Synthesis of compound 31

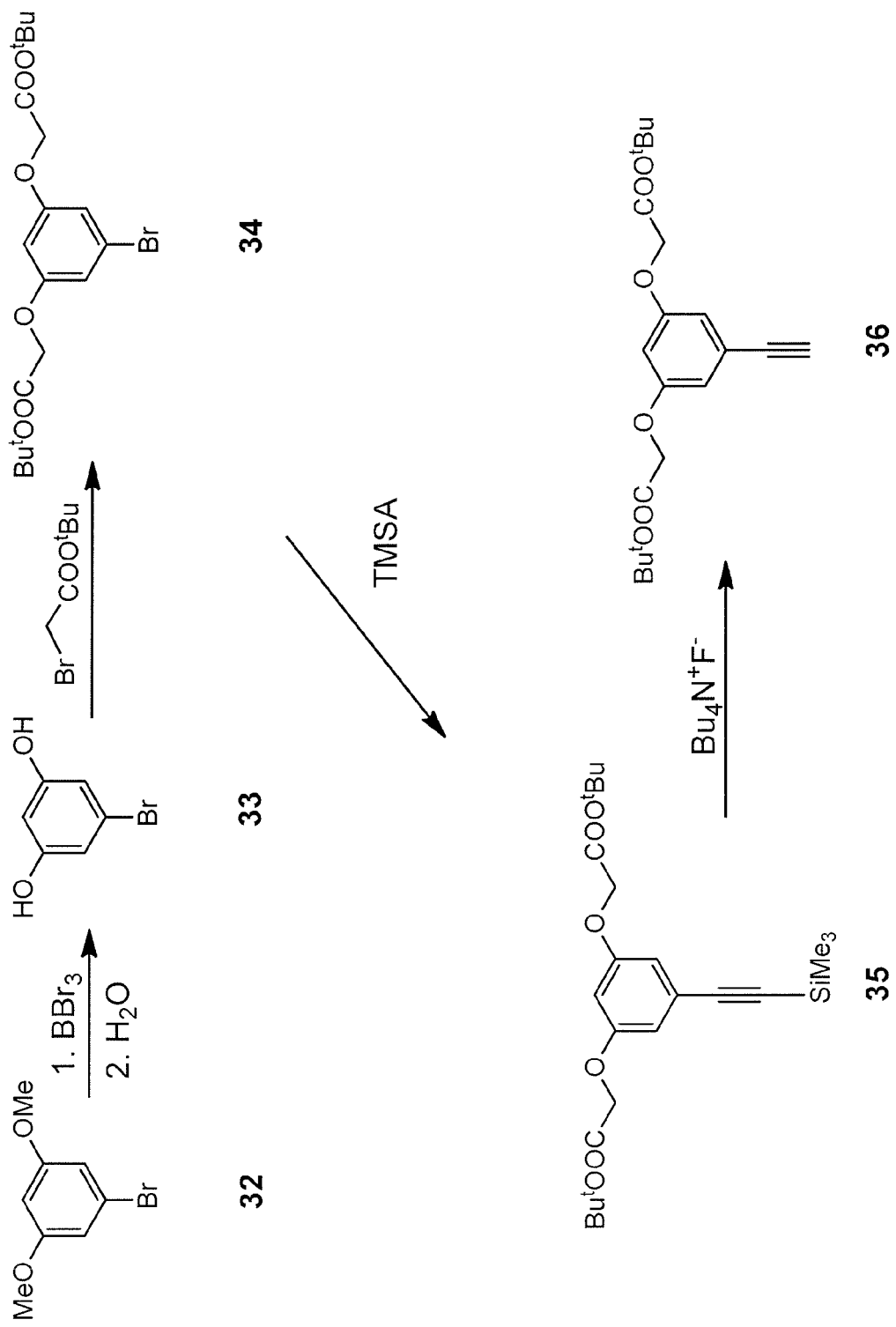
Figure 14. Synthesis of compound 36

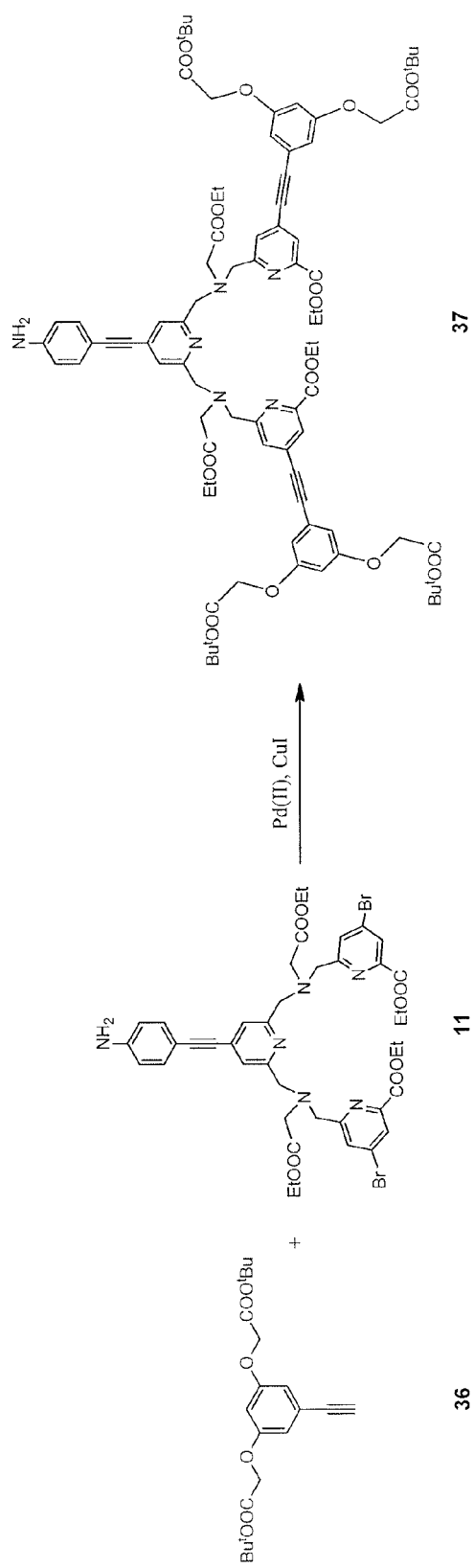
Figure 15. Synthesis of compound 37

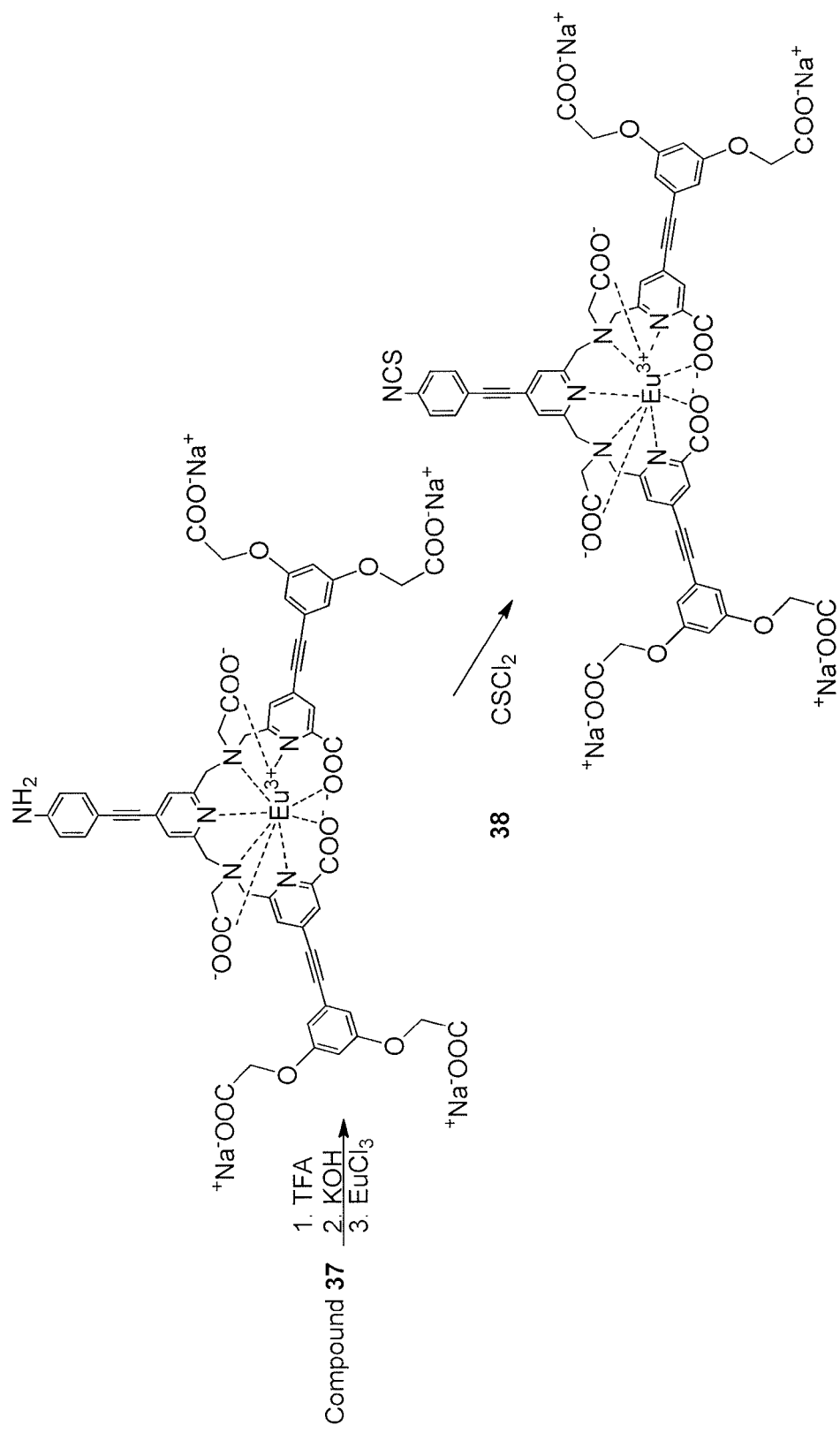
Figure 16. Synthesis of compound 39

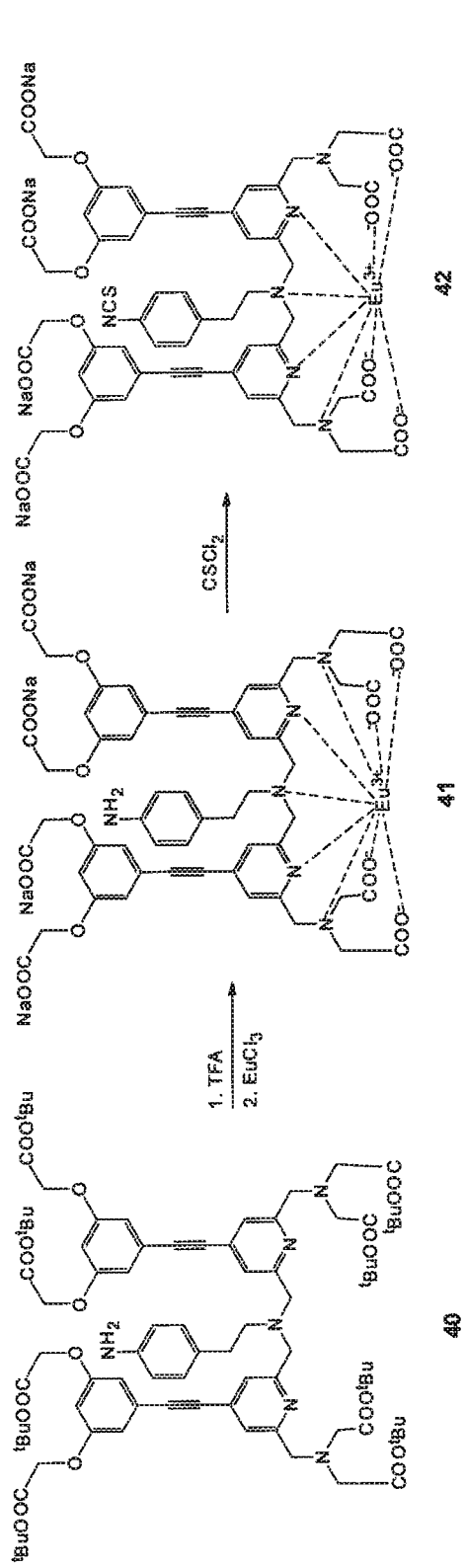
Figure 17. Synthesis of compound 42
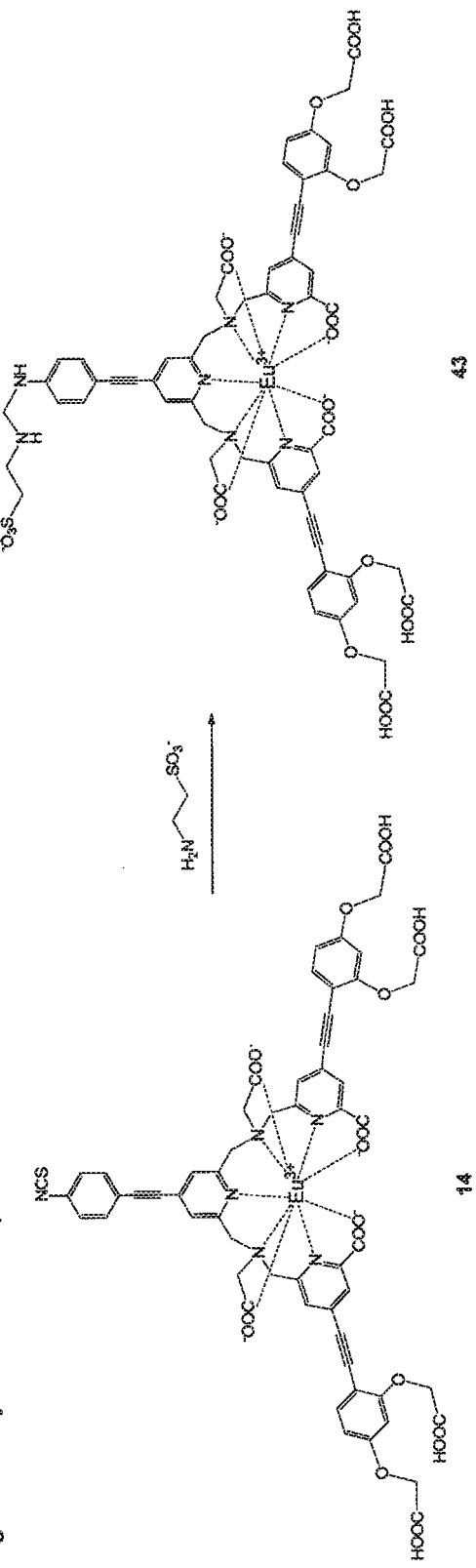
Figure 18. Synthesis of compound 43

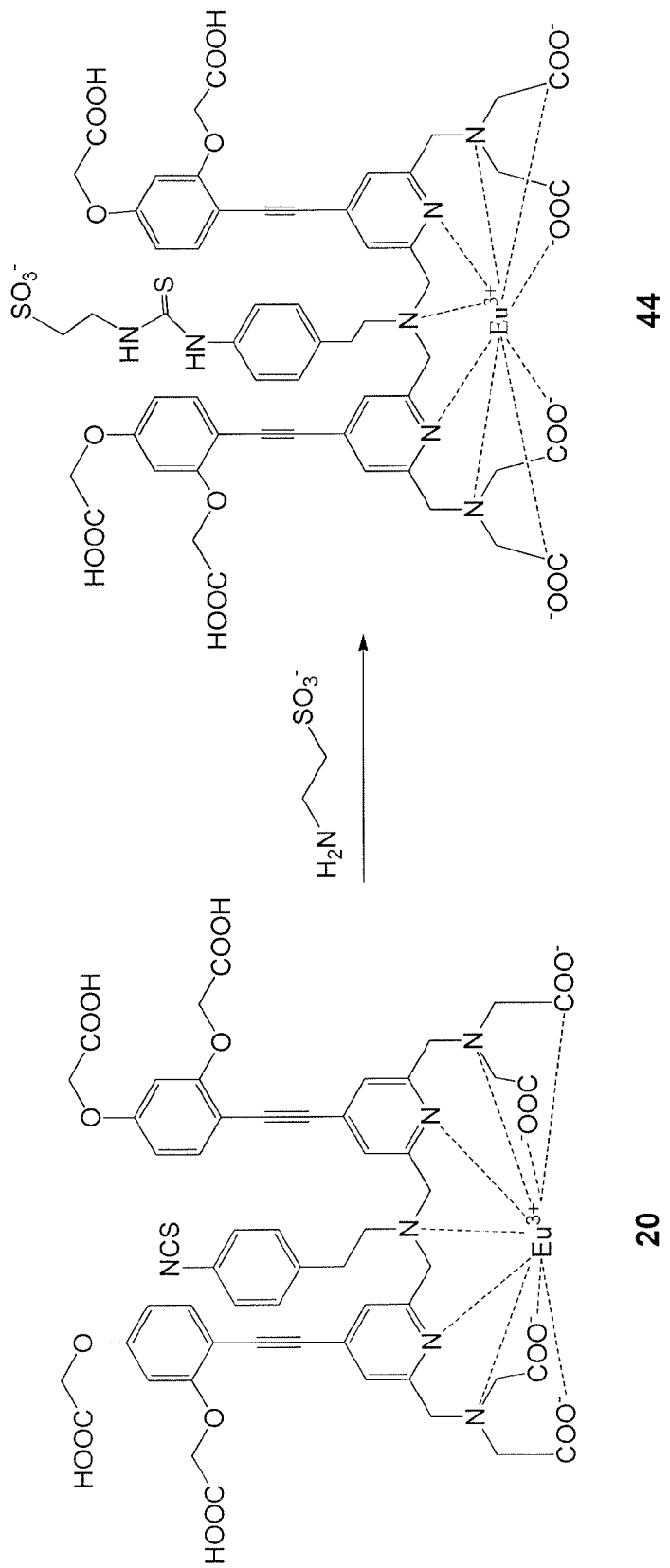
Figure 19. Synthesis of compound 44

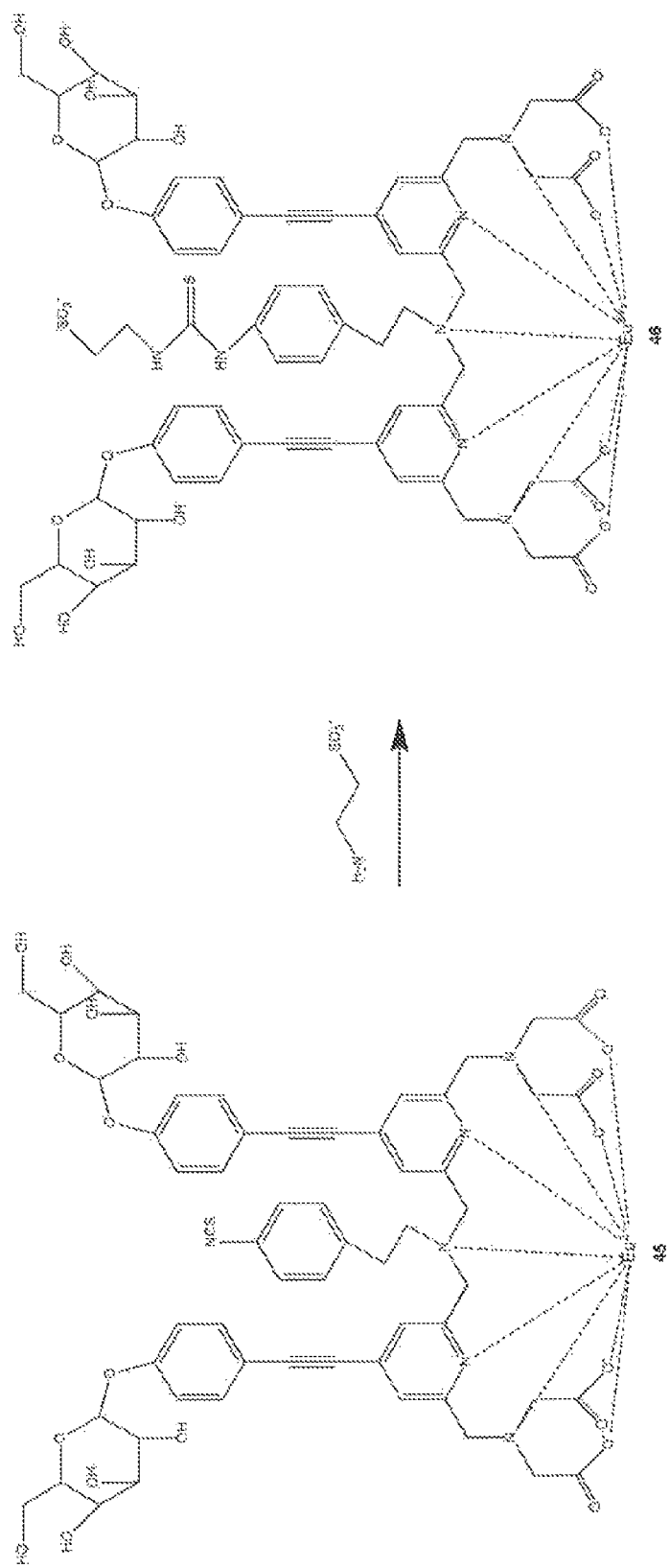
Figure 20. Synthesis of compound 46

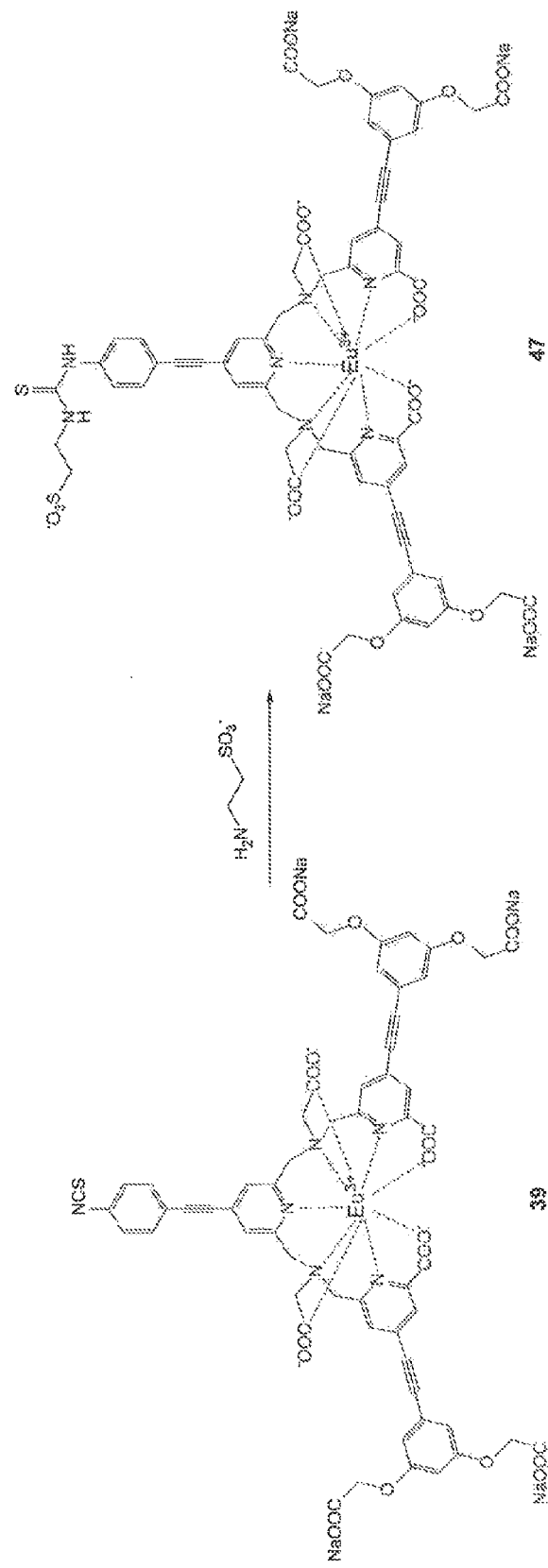
Figure 21. Synthesis of compound 47

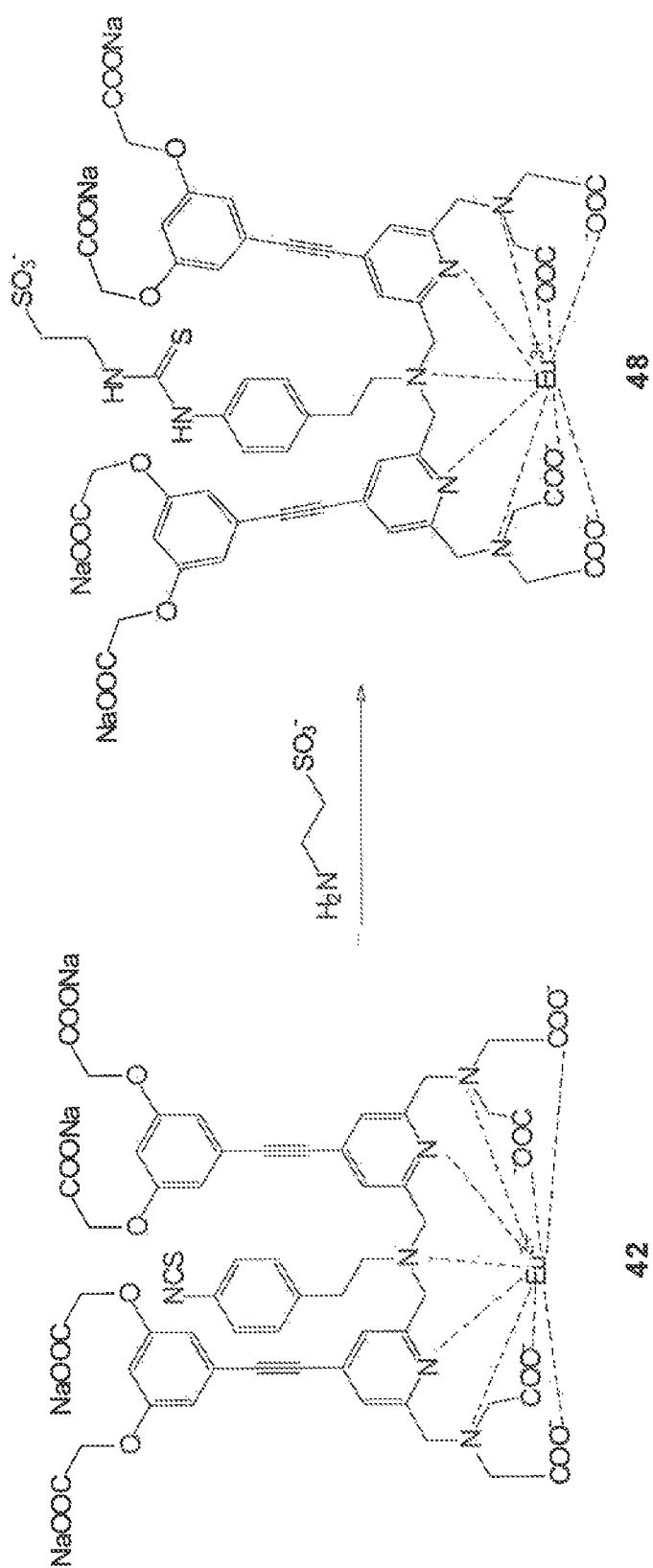
Figure 22. Synthesis of compound 48

LUMINESCENT LANTHANIDE CHELATES WITH ENHANCED EXCITATION PROPERTIES

CROSS-REFERENCE TO RELATED APPLICATIONS

This application claims priority to U.S. Provisional Application No. 61/578,977, filed on Dec. 22, 2011, Denmark Application No. PA2011/00996, filed on Dec. 22, 2011, and PCT Application No. PCT/EP2012/066082, filed Aug. 17, 2012. all of which are incorporated herein by reference.

The disclosure relates to a novel lanthanide chelate design having substituted phenylethynyl pyridine chromophores around an emitting lanthanide ion. The substitution pattern in the phenylethynyl chromophores shifts the excitation spectrum to longer wavelengths and thereby enables efficient excitation of the lanthanide ion at wavelengths higher than 340 nm. The disclosure also relates to chelates to be attached to a biospecific reactant and their use in various assays.

BACKGROUND

Time-resolved fluorometry (TRF) employing long lifetime emitting luminescent lanthanide chelates has been applied in many specific binding assays, such as e.g. immunoassays, DNA hybridization assays, receptor-binding assays, enzymatic assays, bio-imaging such as immunocytochemical, immunohistochemical assays or cell based assays to measure target analytes at very low concentration. Moreover, lanthanide chelates have been used in magnetic resonance imaging (MRI) and position emission tomography (PET).

For TRF application, an optimal label has to fulfill several requirements. First, it has to be photochemical stable both in the ground state and in the excited state and it has to be kinetically and chemically stable. The excitation wavelength has to be as high as possible, preferable over 300 nm. It has to have efficient cation emission i.e. high luminescence yield (excitation coefficient×quantum yield, $\epsilon\Phi$). The observed luminescence decay time has to be long, and the chelate has to have good water solubility. For labeling, it should have a reactive group to allow covalent attachment to a biospecific binding reactant, and the affinity and nonspecific binding properties of the labeled biomolecules have to be retained.

Although shifting of excitation wavelength has been successfully employed in scientific literature, the problem of existing technologies has been that the energy transfer from the chromophore to the lanthanide on has been relatively weak. In other words shifting of excitation wavelength to longer wavelengths has typically been accompanied by weakening of the emission intensity. A majority of the published structures are also unsuitable to be used in aqueous environment i.e. not suitable to be used as labelling reagents in bioaffinity assays.

Knapton et al., "Fluorescent Organometallic Sensors for the Detection of Chemical-Warfare-Agent Mimics", Angew. Chem. Int. Ed. 2006, 45, 5825-5829, discloses a water-insoluble 2,4-dimethoxyphenylethynylenepyridine.

WO 2008/020113 A1 discloses luminescent lanthanide labelling reagents, e.g. 2,2',2",2"'-{[2-(4-isothiocyanatophenypethyl)ethylimino]bis(methylene)bis{4-[2-methoxy-4-(carboxymethoxy)phenyl]pyridine-6,2-diyl}bis(methylenenitrilo)}-tetrakis(acetato)}terbium(III) and their use.

The structures according to the present disclosure provide a general method for shifting the excitation wavelength to above about 340 nm without compromising the chelate performance, i.e. with respect to luminescence yield. The present disclosure enables the use of cheap UV LEDs as an excitation source. Currently 365 nm UV LEDs with sufficient excitation energy are available and the excitation spectrum of the chelates according to the present disclosure strongly suggests the applicability of these chelates in combination with such UV LEDs. Application of LEDs in the instrument design enables cost reduction and miniaturization of the instrument.

Also, the structures according to the disclosure offers highly luminescent water soluble chelate structures with high excitation wavelength although the chromophore(s) has substituted alkoxy substituents in both mesomeric orto- and para-positions. The adsorption properties of the chromophore moieties are decreased due to the additional hydrophilic groups near to the long aromatic π-electron containing structure. This means that these labels should not suffer from increased background although even three independent chromophores are present in the ligand structure.

BRIEF DESCRIPTION OF THE DRAWINGS

FIG. 3 shows the synthesis of compound 4, according to an embodiment of the present disclosure.

FIG. 4 shows the synthesis of shows the synthesis of compound 10, according to an embodiment of the present disclosure.

FIG. 5 is shows the synthesis of compound 11, according to an embodiment of the present disclosure.

FIG. 6 is shows the synthesis of compound 12, according to an embodiment of the present disclosure.

FIG. 7 is shows the synthesis of compound 14, according to an embodiment of the present disclosure.

FIG. 8 is shows the synthesis of compound 20, according to an embodiment of the present disclosure.

FIG. 9 is shows the synthesis of compound 23, according to an embodiment of the present disclosure.

FIG. 10 is shows the synthesis of compound 27, according to an embodiment of the present disclosure.

FIG. 11 is shows the synthesis of compound 28, according to an embodiment of the present disclosure.

FIG. 12 is shows the synthesis of compound 30, according to an embodiment of the present disclosure.

FIG. 13 is shows the synthesis of compound 31, according to an embodiment of the present disclosure.

FIG. 14 is shows the synthesis of compound 36, according to an embodiment of the present disclosure.

FIG. 15 is shows the synthesis of compound 37, according to an embodiment of the present disclosure.

FIG. 16 is shows the synthesis of compound 39, according to an embodiment of the present disclosure.

FIG. 17 is shows the synthesis of compound 42, according to an embodiment of the present disclosure.

FIG. 18 is shows the synthesis of compound 43, according to an embodiment of the present disclosure.

FIG. 19 is shows the synthesis of compound 44, according to an embodiment of the present disclosure.

FIG. 20 is shows the synthesis of compound 46, according to an embodiment of the present disclosure.

FIG. 21 is shows the synthesis of compound 47, according to an embodiment of the present disclosure.

FIG. 22 is shows the synthesis of compound 48, according to an embodiment of the present disclosure.

SUMMARY

Figure 1:
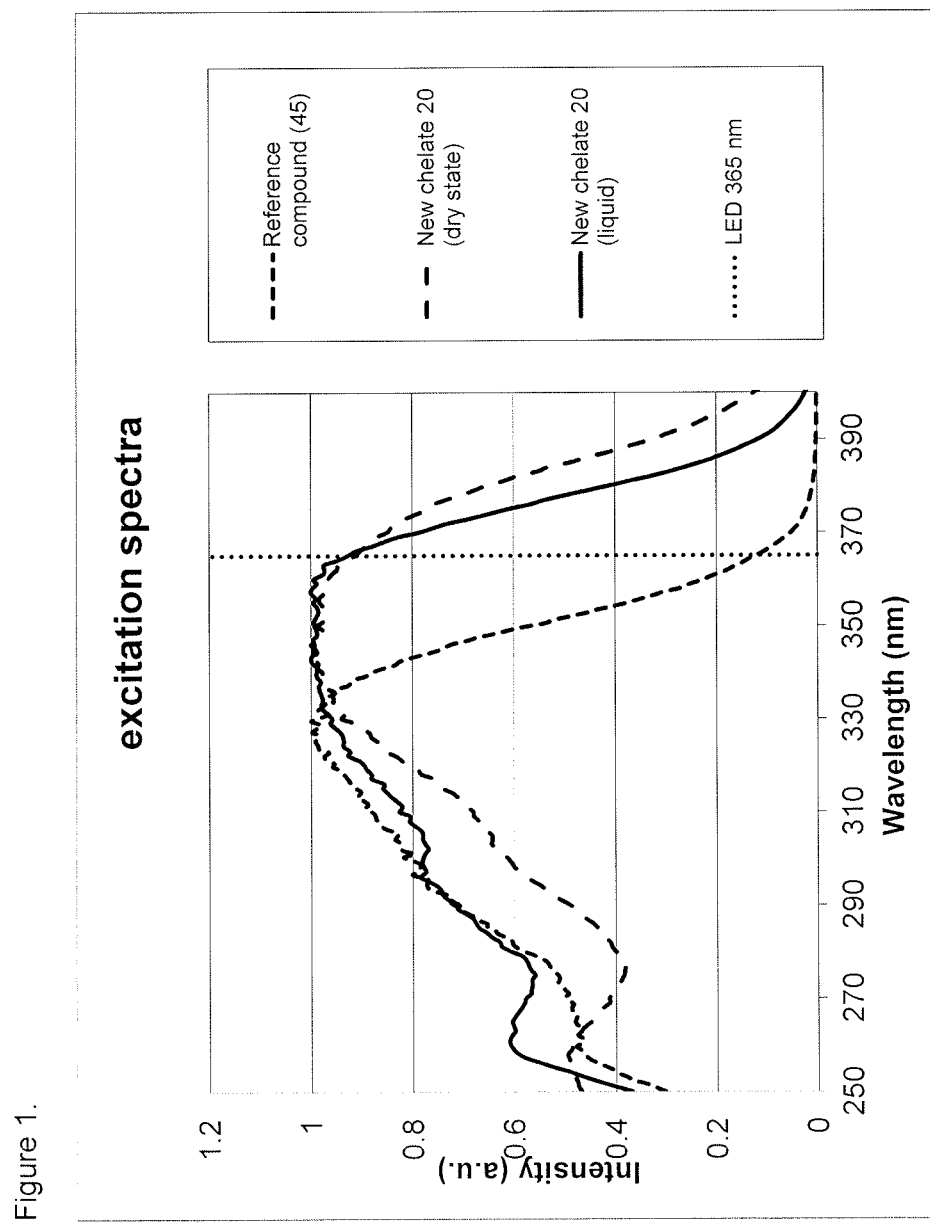
FIG. 1 shows the comparison of the excitation spectrum of a chelate according to an embodiment of the present disclosure, measured both in liquid phase and in dry state, and to the excitation spectrum of reference compound (45).

A first aspect of the Disclosure relates to a luminescent lanthanide chelate comprising one or more chromophoric moieties of the formula (I) or of the formula (III)

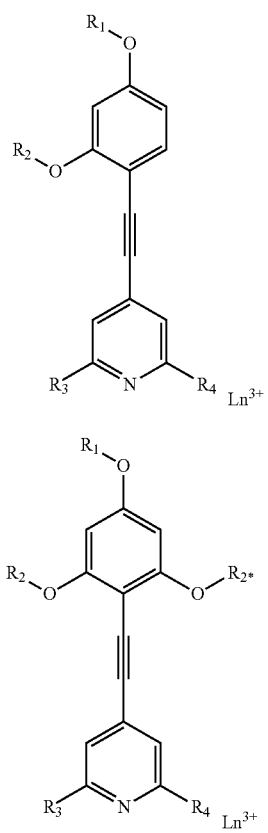

Formula (I)

Formula (III)

A second aspect of the disclosure relates to a detectable molecule comprising a biospecific binding reactant conjugated to a luminescent lanthanide chelate comprising one or more moieties of the formula (I) as defined herein.

A third aspect of the disclosure relates to a luminescent lanthanide chelating ligand comprising one or more chromophoric moieties of the formula (II) or of the formula (IV)

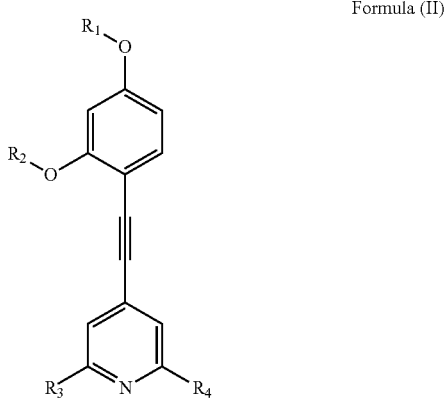

Formula (II)

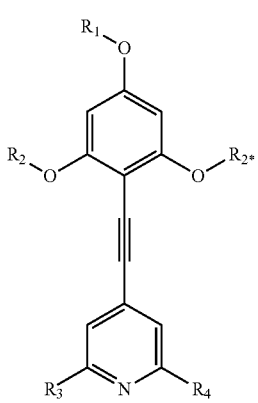

Formula (IV)

A fourth aspect of the disclosure relates to a method of carrying out a biospecific binding assay, said method comprising the steps of: a) forming a biocomplex between an analyte and a biospecific binding reactant labelled with a luminescent lanthanide chelate as defined herein: b) exciting said biocomplex with radiation having an excitation wavelength, thereby forming an excited biocomplex; and c) detecting emission radiation emitted from said excited biocomplex.

A fifth aspect of the disclosure relates to the use of a detectable molecule as defined herein in a specific bioaffinity based binding assay utilizing time-resolved fluorometric determination of a specific luminescence.

A sixth aspect of the disclosure relates to a solid support material conjugated with a luminescent lanthanide chelate as defined herein.

The structural modification according to the present disclosure has been employed in several different chelate structures (14, 20 and 30; see the Examples). For these chelates where the modification was introduced, a more than 20 nm shift of the excitation spectrum was observed compared to chelates having a conventional substitution pattern.

One aspect of the present disclosure relates to a luminescent lanthanide chelate comprising one or more chromophoric moieties of the formula (I) or of the formula (III)

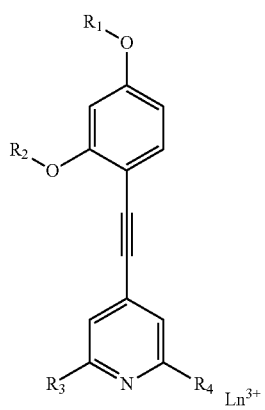

Formula (I)

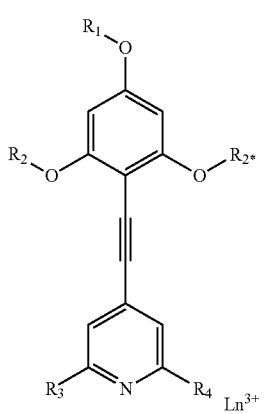

Formula (III)

wherein $R_1$, $R_2$ and $R_{2*}$, when present, each independently are selected from carbon-containing substituents forming a C—O bond with the neighboring oxygen atom, $R_3$ and $R_4$ each represent a bond between the chromophoric moiety and other moieties of the chelate, and $Ln^{3+}$ is a lanthanide ion.

It has been found that the 2,4-(R—O)-substituent configuration (i.e. formula (I)) as well as the 2,4,6-(R—O)-substituent configuration (i.e. formula (III)) provide a significant shift in the excitation spectrum to longer wavelengths compared to a reference chelate of an otherwise similar type, but with nor or little reduction in the emission intensity.

The substituents $R_1$, $R_2$ and $R_{2*}$ each independently are selected from certain carbon-containing substituents forming a C—O bond with the neighboring oxygen atom. It is believed that the specific substituent configuration combined with the substituent type (R—O) is responsible for the observed effect. On the other hand, the substituents $R_1$, $R_2$ and $R_{2*}$ are believed to render the lanthanide chelate comparably more water-soluble and are believed to reduce the unspecific binding properties and thereby reduce the background signal.

Hence, $R_1$, $R_2$ and $R_{2*}$, when present, are each independently selected from —$(CH_2)_{1-6}COOH$, —$(CH_2)_{1-6}COO$—, —$(CH_2)_{1-6}SO_3H$, —$(CH_2)_{1-6}SO_3$—, —$(CH_2CH_2O)_{1-4}OCH_2CH_2OH$, —$(CH_2CH_2O)_{1-4}OCH_2CH_2OCH_3$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)NCH_3R_5$, —$(CH_2)_{1-6}NHC(=O)NHR_5$, —$(CH_2)_{1-6}NHC(=S)NHR_5$, —$(CH_2)_{1-6}C(=O)R_5$, and —$(CH_2)_{1-6}-C_6H_4-R_5$, wherein $R_5$ is selected from hydrogen, $C_{1-12}$-alkyl (in particular $C_{1-6}$-alkyl), —$(CH_2)_{1-6}COOH$, —$(CH_2)_{1-6}COO$—, —$(CH_2)_{1-6}SO_3H$, —$(CH_2)_{1-6}SO_3$—, a hydrophilic group (optionally including a spacer), a reactive group (optionally including a spacer), a polypeptide, and a polynucleotide. In one embodiment, $R_1$, $R_2$ and $R_{2*}$, when present, are each independently selected from —$(CH_2)_{1-6}COOH$, —$(CH_2)_{1-6}COO$—, —$(CH_2)_{1-6}SO_3H$, —$(CH_2)_{1-6}SO_3$—, —$(CH_2CH_2O)_{1-4}OCH_2CH_2OH$ and —$(CH_2CH_2O)_{1-4}OCH_2CH_2OCH_3$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)NCH_3R_5$, —$(CH_2)_{1-6}NHC(=O)NHR_5$, —$(CH_2)_{1-6}NHC(=S)NHR_5$, —$(CH_2)_{1-6}C(=O)R_5$, wherein $R_5$ is selected from hydrogen, $C_{1-12}$-alkyl (in particular $C_{1-6}$-alkyl), —$(CH_2)_{1-6}COOH$, —$(CH_2)_{1-6}COO$—, —$(CH_2)_{1-6}SO_3H$, and —$(CH_2)_{1-6}SO_3$—.

In another embodiment, one of $R_1$, $R_2$ and $R_{2*}$, when present, is —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)NCH_3R_5$, —$(CH_2)_{1-6}NHC(=O)NHR_5$, —$(CH_2)_{1-6}NHC(=S)NHR_5$, —$(CH_2)_{1-6}C(=O)R_5$, and —$(CH_2)_{1-6}-C_6H_4-R_5$, wherein $R_5$ is a reactive group (optionally including a spacer), in particular $R_5$ is —NCS, while the other of $R_1$, $R_2$ and $R_{2*}$, when present, are as defined above, except that any $R_5$ is not a reactive group. In one variant hereof, one of $R_1$, $R_2$ and $R_{2*}$, when present, is —$(CH_2)_{1-6}-C_6H_4-NCS$, in particular —$CH_2-C_6H_4-NCS$.

It is presently believed that some types of substituents, i.e. those of the carboxylic add and sulfonic add type, are especially interesting. Hence, in a preferred embodiment, $R_1$, $R_2$ and $R_{2*}$ (when present) are each independently selected from —$(CH_2)_{1-6}COOH$, —$(CH_2)_{1-6}COO$—, —$(CH_2)_{1-6}SO_3H$, and —$(CH_2)_{1-6}SO_3$—, in particular from —$CH_2$-COOH and —$CH_2$-COO—.

In one embodiment $R_1$, $R_2$ and $R_{2*}$ (when present) are each independently selected from —$CH_2$-COOH and —$CH_2$-COO.

In one embodiment, the one or more chromophoric moieties are of the formula (I), i.e. having a 2,4-substitution pattern. It is believed that such a substitution pattern provides a reduction of the unspecific binding properties (reduction of the background signal).

In another embodiment, the one or more chrornophoric moieties of the formula (III), i.e. having a 2,4,6-substitution pattern. It is believed that such a substitution pattern provides a reduction of the unspecific binding properties (reduction of the background signal.

When the substituents are carboxylates, sulfonates and the like, the chelates may include cations as counter ions, e.g. $Na^+$, $K^+$, $Ca^{2+}$ and the like. When present, any hydrophilic groups can help improve water solubility of the chelate.

Examples of hydrophilic groups are mono- and oligosaccharides, such as monosaccharides and disaccharides, oligoalkylene glycols (e.g. those having 1-20 repeating units) such as oligoethylene glycol and oligopropylene glycol, etc. In one embodiment, the hydrophilic group is selected from monosaccharides, disaccharides, —$C(CH_2OH)_3$, —$(CH_2)_{1-3}$—O—$(CH_2CH_2O)_{0-5}$—H, —$(CH_2)_{1-3}$—O—$(CH_2CH_2O)_{0-5}$—$C_{1-4}$-alkyl, —O—$(CH_2CH_2O)_{1-6}$—H, and —O—$(CH_2CH_2O)_{1-6}$—$C_{1-4}$-alkyl, in particular monosaccharides.

In the present context, the term "monosaccharide" is intended to mean $C_5$-$C_7$ carbohydrates being either in the acyclic or in cyclic form. Examples of monosaccharides are $C_6$ carbohydrates, e.g. those selected from

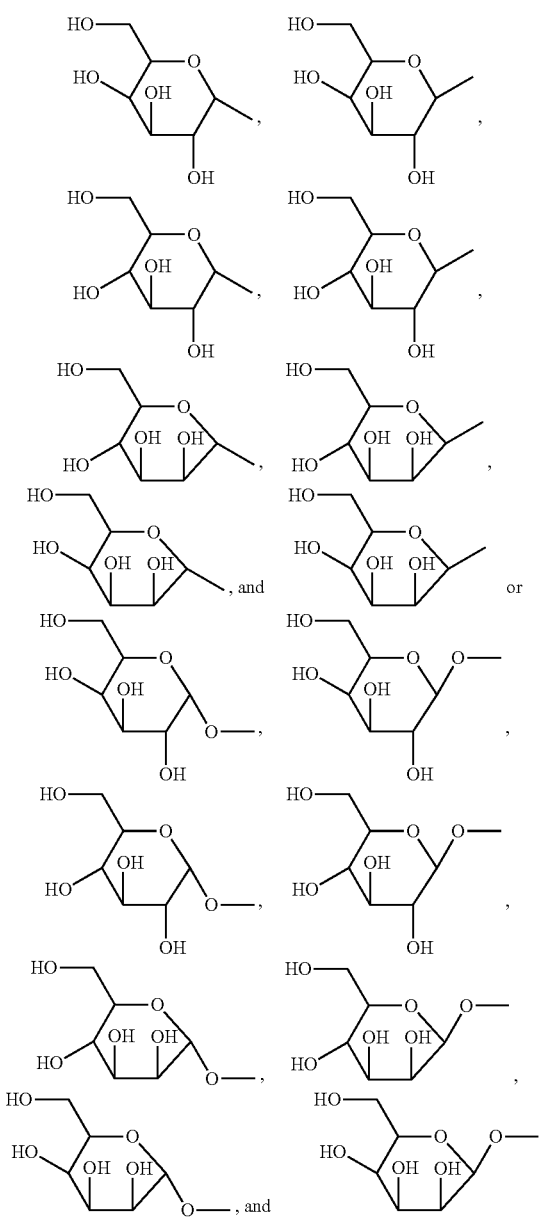

In the present context, the term "disaccharide" is intended to mean two monosaccharides (cf. above) linked together, preferably via glycosidic bonds.

In other possible embodiments, a hydrophilic group is present in the chelate structure, but not in the chromophoric moiety of formula (I).

In some alternative embodiments, the substituent $R_1$ and/or $R_2$ and/or $R_{2*}$ includes a reactive group Z, preferably including a spacer. In such instances, the reactive group Z is facilitating the labeling of a biospecific binding reactant or is facilitating the formation of a covalent bond to a solid support material. In case the chelate has a polymerizing group as reactive group, then the chelate may be introduced in the solid support, e.g. a particle, simultaneously with the preparation of the particles.

If present, the reactive group Z is typically selected from azido (—$N_3$), alkynyl (—C≡CH), alkylene (—CH=$CH_2$), amino (—$NH_2$), aminooxy (—O—$NH_2$), carboxyl (—COOH), aldehyde (—CHO), mercapto (—SH), maleimido, activated derivatives of maleimido, isocyanato (—NCO), isothiocyanato (—NCS), diazonium (—$N^+N$), bromoacetamido, iodoacetamide, reactive esters, pyridyl-2-dithio, and 6-substituted 4-chloro-1,3,5-triazin-2-ylamino, in particular, the reactive group comprises a isothiocyanato (—NCS) group. The substituents in 6-substituted 4-chloro-1,3,5-triazin-2-ylamino can be selected from the group consisting hydrogen, halogen, alkoxy, aryloxy, amino, alkyl with one to six carbon atoms, substituted amino or thioethers, and preferable selected from the group consisting of chloro, fluoro, ethoxy, 2-methoxyethoxy, 2-cyanoethoxy, 2,2,2-trifluoroethoxy, thiophenoxy or ethoxycarbonyl-thiomethoxy. The substituted amino or thioether is preferable mono- or disubstituted each substituent being preferable independently selected from the group consisting of an alkyl or alkoxy with one to six carbon atoms, phenyl, carbonyl or carboxyl.

It follows that upon reaction with a biospecific binding reactant (see further below), the reactive group Z establishes a link to said biospecific binding reactant, e.g. of one of the following types: a thiourea (—NH-C(=S)-NH—), an aminoacetamide (—NH-CO-$CH_2$-NH—), an amide (—NH-CO—, —CO-NH—, —$NCH_3$-CO— and —CO-$NCH_3$—), and aliphatic thioether (—S—), a disulfide (—S-S—), a 6-substituted-1,3,5-triazine-2,4-diamine, a

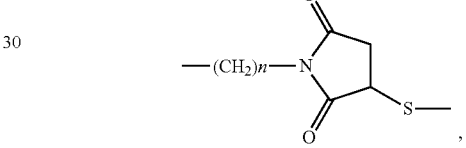

wherein n=1-6; and a triazole (e.g. formed by the so-called "click" chemistry).

In other possible embodiments, a reactive group Z (as specified) is present in the chelate structure, but not in the chromophoric moiety of formula (I).

When a reactive group Z is present, the group Z may include a spacer, i.e. a distance-making biradical to position the reactive group Z in a position accessible for reaction with the biospecific binding reactant if necessary or desired. Similarly, when any of $R_1$, $R_2$ and $R_{2*}$ include a hydrophilic group, the hydrophilic group may include a spacer. In both instances, the spacer may be readily introduced in the course of the synthesis of the ligand or the chelate.

The term "space" is intended to mean a distance-making group between, e.g., a conjugating group or a pyridine moiety of the core structure and, e.g. the reactive group Z or a hydrophilic group. The spacer typically has a length of 1-20 bonds between the attachment point and reactive group (or hydrophilic group), such as 3-15 bonds, or 5-12 bonds. The spacer is formed of one to five moieties, each moiety selected from the group consisting of phenylene, alkylene containing 1-10 carbon atoms, an ethynediyl (—C≡C—), an ether (—O—), a thioether (—S—), a disulfide (—S-S—), an amide (—C(=O)-NH—, —NH-C(=O)—, —C(=O)-$NCH_3$— and —$NCH_3$-C(=O)—), a thiourea (—NH-C(=S)-NH—) and a triazole.

In some embodiments, at least one of the substituents $R_1$ and/or $R_2$ and/or $R_{2*}$ include apolypeptide or a polynucleotide.

$R_3$ and $R_4$ each represent a bond between the chromophoric moiety and other moieties of the chelate, e.g. chromophoric moieties and chelating moieties.

The chelating moity comprising at least two carboxylic acid or phosphoric acid groups, ester, amides or salts of said acids, attached to an aromatic unit of the chromophoric moiety, either directly or via a cyclic or acyclic N- and/or O-containing hydrocarbon chain. It should be understood that the chromophoric moiety of formula (I) or (II) may replace any phenylethynylpyridine moiety in conventional chelates. Hence, it is appreciated that the chromophoric moiety can be incorporated in conventional chelates having other chromophoric moieties either similar or different to the chromophoric moiety of formula (I) or (II). Illustrative examples are provided in the examples section.

$R_3$ and $R_4$ each represent a bond to other moieties of the chelate, e.g. to another chromophoric moiety, typically via a linker, or to a complexing group (e.g. —COOH/—COO—), or simply to an end group or a hydrogen atom.

In some embodiments, the chelate has a total of two or three chromophoric groups. Exemplary embodiments are illustrated with the Formulas (A) and (B).

The term "lanthanide ion" or "$Ln^{3+}$" is intended to mean a trivalent ion of the lanthanide series of the Periodic Table of Elements, e.g. europium(III), terbium(III), samarium(III) and dysprosium(III), i.e. $Eu^{3+}$, $Tb^{3+}$, $Sm^{3+}$ or $Dy^{3+}$. In many embodiments europium(III) ($Eu^{3+}$) is preferred.

In one embodiment, the disclosure provides highly luminescent labels for all lanthanides, which provides multi-label possibilities.

In some embodiments, the chelate has one of the structural formulae (A-I), (A-II), (B-I) and (B-II) below:

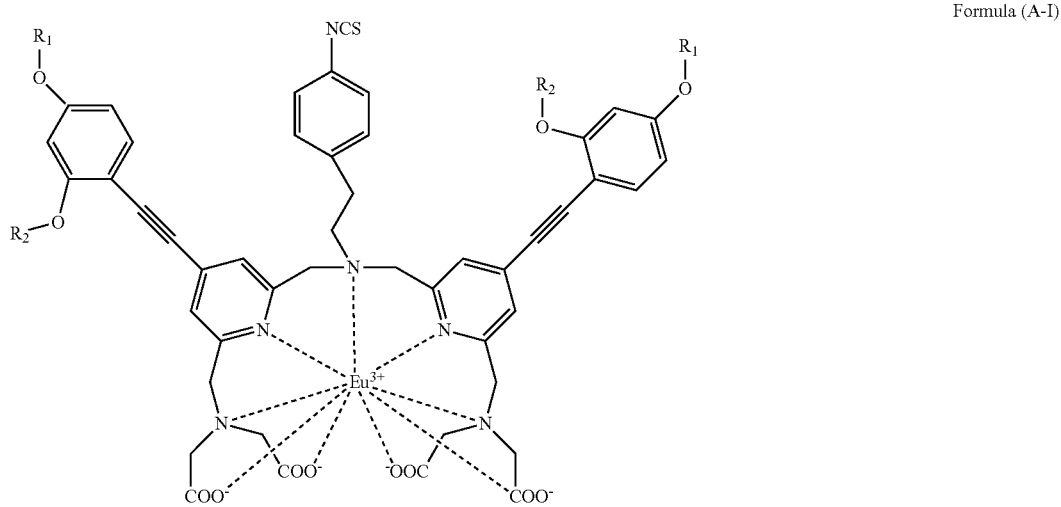

Formula (A-I)

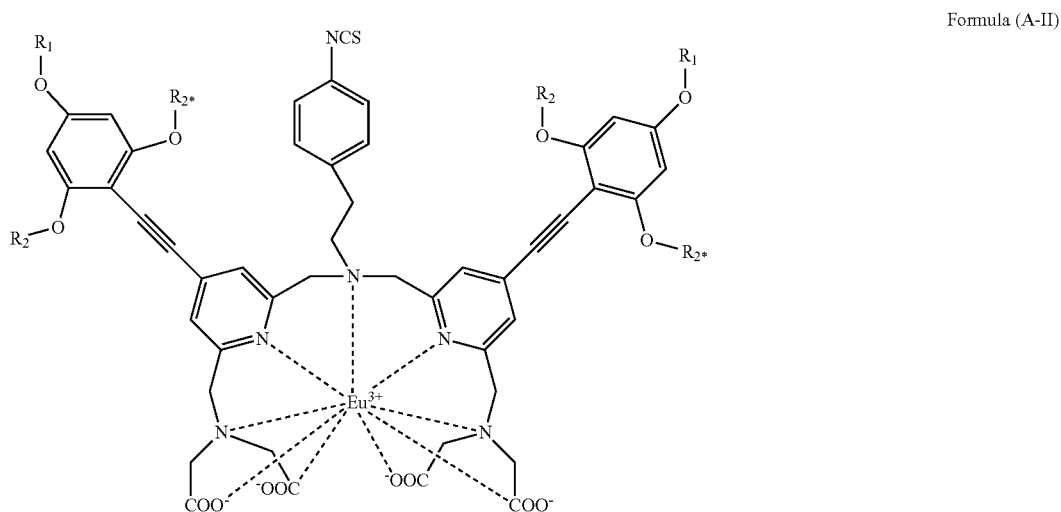

Formula (A-II)

-continued

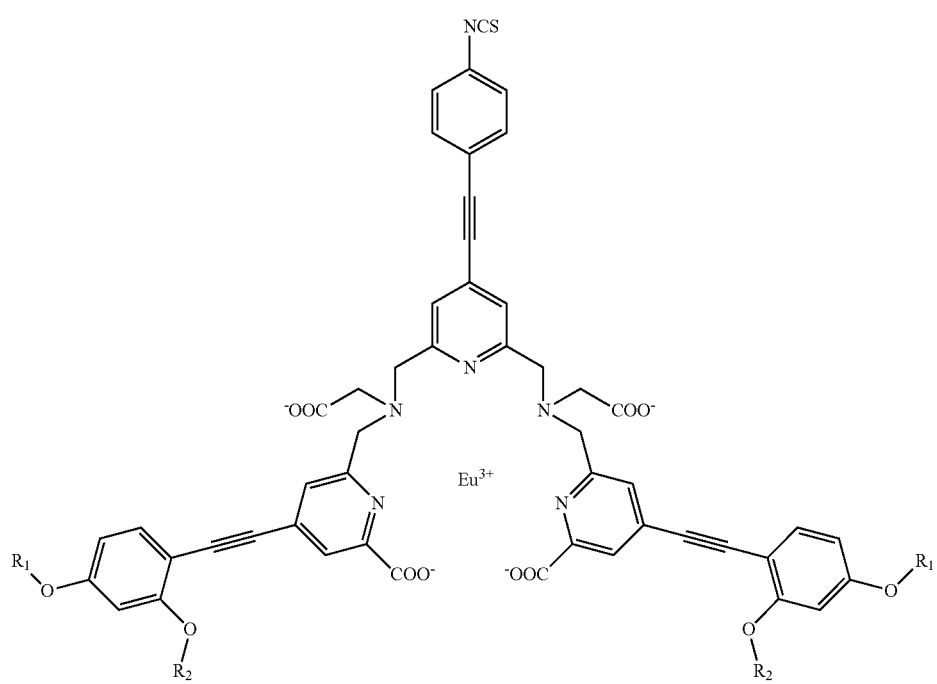

(Formula B-I)

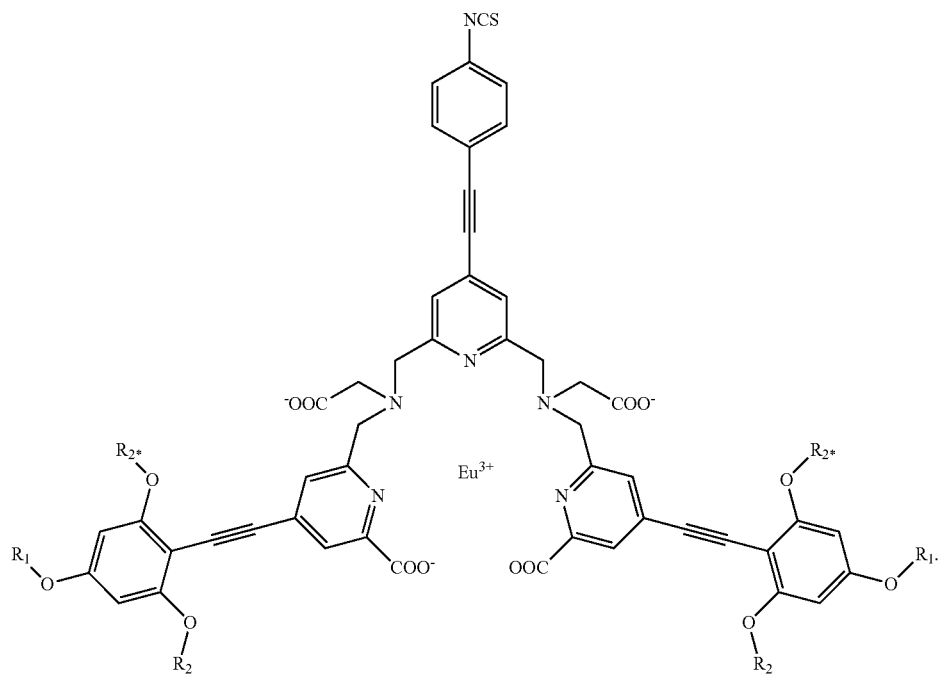

Formula (B-II)

In each of the formulas (A-I), (A-II), (B-I) and (B-II), the substituents $R_1$, $R_2$ and $R_{2*}$, when present, may each independently be selected from —$(CH_2)_{1-6}$COOH, —$(CH_2)_{1-6}$COO—, —$(CH_2)_{1-6}$SO$_3$H, —$(CH_2)_{1-6}$SO$_3$—, —$(CH_2CH_2O)_{1-4}$OCH$_2$CH$_2$OH, —$(CH_2CH_2O)_{1-4}$OCH$_2$CH$_2$OCH$_3$, —$(CH_2)_{1-6}$NHC(=O)R$_5$, —$(CH_2)_{1-6}$NCH$_3$C(=O)R$_5$, —$(CH_2)_{1-6}$C(=O)NHR$_5$, —$(CH_2)_{1-6}$C(=O)NCH$_3$R$_5$, —$(CH_2)_{1-6}$NHC(=O)NHR$_5$, —$(CH_2)_{1-6}$NHC(=S)NHR$_5$, and —$(CH_2)_{1-6}$C(=O)R$_5$, wherein $R_5$ is selected from hydrogen, $C_{1-12}$-alkyl, —$(CH_2)_{1-6}$COOH, —$(CH_2)_{1-6}$COO—, —$(CH_2)_{1-6}$SO$_3$H, —$(CH_2)_{1-6}$SO$_3$—, a hydrophilic group (optionally including a spacer), a reactive group (optionally including a spacer), a polypeptide and a nucleotide.

In one preferred embodiment, the chelate has the formula (A-I) or (B-I) and $R_1$ and $R_2$ are each independently selected from —$(CH_2)_{1-6}$COOH, —$(CH_2)_{1-6}$COO—, —$(CH_2)_{1-6}$SO$_3$H, and —$(CH_2)_{1-6}$SO$_3$—, in particular from —CH$_2$-COOH and —CH$_2$-COO—.

In another preferred embodiment, the chelate has the formula (A-II) or (B-II) and $R_1$, $R_2$ and $R_{2*}$ are each independently selected from —(CH$_2$)$_{1-6}$COOH, —(CH$_2$)$_{1-6}$COO—, —(CH$_2$)$_{1-6}$SO$_3$H, and —(CH$_2$)$_{1-6}$SO$_3$—, in particular from —CH$_2$-COOH and —CH$_2$-COO—.

In one embodiment, Eu$^{3+}$ is preferred in formula (A) and (B). In other embodiments, Eu$^{3+}$ may be replaced by any other lanthanide selected from Tb$^{3+}$, Sm$^{3+}$ and Dy$^{3+}$.

In some embodiments, the disclosure is directed to lanthanide chelates of any one of the formulas 13, 14, 43, 19, 20, 44, 29, 30, and 31.

In another aspect, the present disclosure relates to a lanthanide chelating ligand comprising one or more chromophoric moieties of the formula (II) or of the formula (IV)

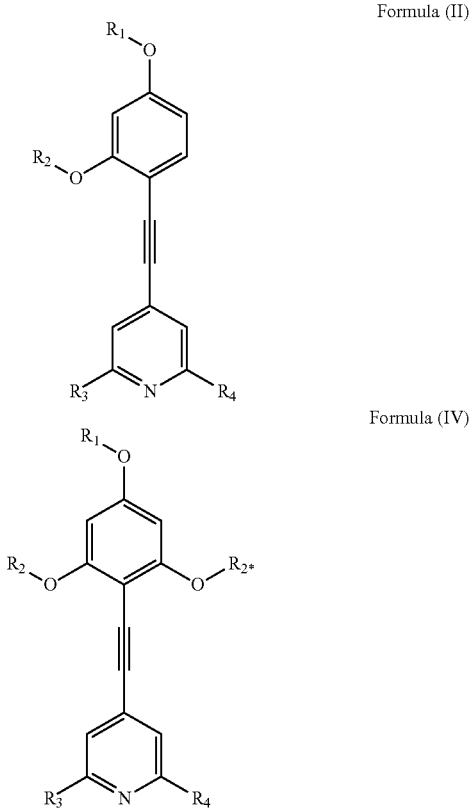

Formula (II)

Formula (IV)

wherein each of R$_1$, R$_2$, R$_{2*}$, R$_3$, and R$_4$ represents the groups R$_1$, R$_2$, R$_{2*}$, R$_3$, and R$_4$, respectively, as defined for formula (I).

In some embodiments, the lanthanide chelating ligand has one of the formulas (A-I) (A-II), (B-I) or (B-II) above (excluding the Eu$^{3+}$). In some embodiments, the present disclosure related to lanthanide chelates ligands with formulas 13, 14, 43, 19, 20, 44, 29, 30, and 31 (excluding the Eu$^{3+}$).

The present disclosure also relates to a detectable molecule comprising a biospecific binding reactant conjugated to a luminescent lanthanide chelate as described above. Conjugation is typically obtained by means of a reactive group of said chelate.

The biospecific binding reactant should be capable of specifically binding an analyte of interest for the purpose of quantitative or qualitative analysis of said analyte in a sample. Non-limiting examples of biospecific binding reactants are those selected from an antibody, an antigen, a receptor ligand, a specific binding protein, a DNA probe, a RNA probe, an oligopeptide, an oligonucleotide, a modified oligonucleotide (e.g. an LNA modified oligonucleotide), a modified polynucleotide (e.g. an LNA modified polynucleotide), a protein, an oligosaccaride, a polysaccharide, a phospholipid, a PNA, a steroid, a hapten, a drug, a receptor binding ligand, and lectine. In a preferred embodiment, the biospecific binding reactant is selected from antibodies, e.g. Troponin I antibodies (anti-TnI).

Another aspect of the disclosure relates to a method of carrying out a biospecific binding assay, wherein the method comprises the steps of:
    forming a biocomplex between an analyte and a biospecific binding reactant labelled with a lanthanide chelate as defined herein
    exciting said biocomplex with radiation having an excitation wavelength, thereby forming an excited biocomplex; and
    detecting emission radiation emitted from said excited biocomplex.

in one embodiment, the excitation wavelength is preferably about 300 nm or longer, for example about 320-360 nm.

The method follows the conventional assay steps as will be evident for the skilled person.

In one embodiment, the disclosure relates to the use of a detectable molecule in a specific bioaffinity based binding assay utilizing time-resolved fluorometric determination of a specific luminescence. In one embodiment, the specific bioaffinity based binding assay is a heterogeneous immunoassay, a homogenous immunoassay, a DNA hybridization assay, a receptor binding assay, an immunocytochemical or an imniunohistochemical assay.

In one embodiment, the disclosure relates to a said support material conjugated with a luminescent lanthanide chelate as defined above. The luminescent lanthanide chelate is typically immobilized to the solid support material either covalently or non-covalently. In some embodiments, the solid support material is selected from a nanoparticle, a microparticle, a slide, a plate, and a solid phase synthesis resin.

The novel lanthanide chelates ligands and the corresponding luminescent lanthanide chelates and labeled biospecific binding reactants are based on an open chain, i.e. acyclic, ligand structure which provides surprisingly efficiently excitation of the chelated lanthanide ion. At the same time, all important features of the luminescent lanthanide chelate and labeled biospecific binding reactant can be retained without any additional formation of aggregates and purification problems.

In one embodiment, the chelates of the present disclosure combine several important features in a single label. For example, the shift towards longer wavelengths enables the use of UV LEDs as an excitation source which will provide a cost reduction in instrument manufacturing, and the possibility of instrument miniaturization. Also, the chelates are applicable to different lanthanides. It is possible to decrease the labeling degree without loss of signal. Another feature relates to the fac that the lower degree of labeling can improve the affinity of the biomolecule and decrease unspecific binding during the assay. Thus faster kinetic is possible and lower background is seen which can also improve the assay sensitivity. In addition, reduction of unwanted adsorption properties of the chromophore moiety with improved aqueous solubility, especially concerning chelates with several aromatic chromophore moieties. This should reduce the unspecific binding of the labeled antibody and give improved assay sensitivity.

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations.

EXAMPLES

By way of non-limiting illustration, concrete examples of certain embodiments of the present disclosure are given below.

$^1$H-NMR spectra were recorded with Bruker AVANCE DRX 500 MHz. Tetramethyl silane was used as internal reference. Mass spectra were recorded on Applied Biosystems QSTAR XL ESI-TOF instrument. UV-Vis spectra were recorded on Pharmacia Ultrospec 3300 pro. Fluorescence efficiencies were determined with Perkin-Elmer Wallac Victor™ plate fluorometer. Column chromatography was performed with columns packed with silica gel 60 (Merck).

Preparation of Compounds

Example 1

Synthesis of diethyl 2,2'-((4-bromo-1,3-phenylene)bis(oxy))diacetate (2)

4-bromoresorcinol (1.00 g, 5.29 mmol) was dissolved in DMF (20 ml, dry). Anhydrous $K_2CO_3$ (4.39 g, 31.74 mmol) and ethyl bromoacetate (2.30 ml, 15.87 mmol) were added. Mixture was stirred overnight at 40° C. under argon atmosphere. Water (30 ml) was added and the mixture was extracted with ethyl acetate (1×20 ml, 2×10 ml). Combined organic extracts were washed with water (2×10 ml), dried over $Na_2SO_4$ and concentrated. Crude product was purified by column chromatography using silica gel as stationary phase and dichloromethane as eluent. Product was a white solid. Yield: 1.70 g (89%) $^1$H NMR (CDCl$_3$, δ ppm): 7.43 (1H, d, J=8.7 Hz), 6.48 (1H, d, J=2.7 Hz), 6.40 (1H, dd, J=8.7 Hz, J=2 7 Hz), 4.66 (2H, s), 4.57 (2H, s), 4.27 (4H, m) 1.30 (6H, m).

Example 2

Synthesis of diethyl 2,2'-((4-((trimethylsilyl)ethynyl)-1,3-phenylene)bis(oxy))diacetate (3)

Compound 2 (1.56 g, 4.33 mmol) was dissolved in DMF (3 ml, dry) and the solution was pieced in a microwave reaction vial. Diethyl amine (9 ml, dry), Pd(PPh$_3$)$_2$Cl$_2$ (152.0 mg, 0.217 mmol), CuI (41.2 mg, 0.217 mmol) and PPh$_3$ (113.6 mg, 0433 mmol) were added and the vial was sealed in an argon atmosphere. Trimethylsiiyi acetylene (925 μl, 6.50 mmol) was added through a septum and the mixture was stirred at 100° C. for 30 minutes using microwave heating. Reaction mixture was filtrated through silica gel using dichloromethane as eluent and the filtrate was evaporated to dryness. The crude product was dissolved in dichloromethane and purified by column chromatography using silica gel as stationary phase and 10% ethyl acetate: petroleum ether as eluent. Yield: 0.99 g (61%) $^1$H NMR (CDCl$_3$, δ ppm): 7.43 (1H, dd, J=1.35 Hz, J=7.55 Hz), 6.43 (2H, m), 4.67 (2H, s), 4.58 (2H, s), 4.27 (4H, m), 1.30 (6H, m), 0.25 (9H, s).

Example 3

Synthesis of diethyl 2,2'-((4-ethynyl-1,3-phenylene)bis(oxy))diacetate (4)

Compound 3 (398.9 mg, 1.054 mmol) was dissolved in dichloromethane (10 ml, dry). Tetrabutyl ammoniumfluoride (330.7 mg, 1.265 mmol) was added and the mixture was stirred in argon atmosphere at room temperature for 1 h 30 min. Mixture was washed with 10% citric acid solution (5 ml), and water (4×10 ml). The organic phase was dried over Na$_2$SO$_4$ and evaporated to dryness. Crude product was purified by column chromatography using silica gel as stationary phase and 15% ethyl acetate:petroleum ether as eluent. Yield: 259.2 mg (80%) $^1$H NMR (CDCl$_3$, δ ppm): 7.40 (1H, d, J=8.35 Hz), 6.45 (1H, d, J=2.4 Hz), 6.43 (1H, dd, J=5.25 Hz, J=2.4 Hz), 4.70 (2H, s), 4.59 (2H, s), 4.27 (4H, m) 3.24 (1H, s), 1.29 (6H, m).

Example 4

Synthesis of 2,6-bis(hydroxymethyl)-4-iodopyridine (6)

Diethyl 4-iodo-2,6-pyridinedicarboxylate (5) (5.57 g, 17.3 mmol) was suspended in ethanol (130 ml), Sodium borohydride (2.95 g, 78 mmol) was added in small portions to the stirred solution during 15 min. The mixture was refluxed for 1 h 30 min and allowed then to cool down to RT. The reaction mixture was evaporated to dryness and the residue was suspended in saturated aqueous sodium hydrogen carbonate (35 ml). The suspension was rapidly boiled up, allowed to cool and evaporated to dryness. The residue was suspended in mixture of DMF and dichloromethane (1:1, 65 ml), filtrated through Celite pad and the filtrate was evaporated to dryness. The product was crystallized from water and dried in vacuum desiccator over silica gel. Yield 3.37 g (60%). 1HNMR (CDCl3, δ ppm): 7.70 (2H, s), 5.46 (2H, s), 4.48 (4H, s).

Compound 5 was prepared as described in Takalo H. and Kankare J., Acta Chemica Scandinavica B 41, 1987, 219-221.

Example 5

Synthesis of 2,6-bis(bromomethyl)-4-iodopyridine(7)

Phosphorus tribromide (2.45 ml, 26 mmol) was added drop-wise to anhydrous DMF (19.5 ml) at 0° C. resulting in a semisolid mixture. 2,6-bis(hydroxymethyl)-4-iodopyridine (6) (3.36 g, 12.7 mmol) was added to the mixture in small portions. The solid mixture solubilizes during the addition. The mixture was allowed to warm up to RT and stirred 4 h at RT. The reaction mixture was poured to 100 ml of aqueous sodium hydrogen carbonate (5%). The precipitated product was collected by filtration, washed with water and dried in vacuum desiccator over silica gel. Yield 4.51 g (91%). 1HNMR (CDCl3, δ ppm): 7.76 (2H, s), 4.45 (4H, s)

Example 6

Synthesis of Compound ethyl-2-((4-bromo-6-(carboxyethyl)-pyridine-2-yl)methylenenitrilo)acetate (9)

4-bromo-6-bromomethyl-2-carboxyethylpyridine (8) (2.99 g, 9.3 mmol) and glycine ethyl ester hydrochloride (6.52 g, 46.7 mmol) were dissolved in mixture of anhydrous acetonitrile (125 ml) and di-isopropylethylamine (16.5 ml). Mixture was stirred overnight at RT. Reaction mixture was evaporated to dryness and the product was purified with column chromatography using silica as a stationary phase and dichloromethane:methanol (3% 97:3) as an eluent. Yield: 2.78 g (86%) 1HNMR (CDCl3, δ ppm): 8.14 (1H, d, J=1.65 Hz), 7.85 (1H, d, J=1.60 Hz), 4.47 (2H, q, J=7.12 Hz), 4.20 (2H, q, J=7.13 Hz), 4.05 (2H, s), 3.47 (2H, s), 2.26 (1H, s), 1.43 (3H, t, J=7.13 Hz), 1.28 (3H, t, J=7.13 Hz).

Compound 8 was prepared as described in Takalo at al., Hely. Chim. Acta, 1996, 79, 789-802.

Example 7

Synthesis of diethyl 6,6'-((((4-iodopyridine-2,6-diyl)bis(methylene))bis((2-ethoxy-2-oxoethyl)azanediyl))bis(methylene))bis(4-bromopicolinate) (10)

Compound 7 (0.94 g, 2.4 mmol) and compound 9 (1.66 g, 4.8 mmol) were dissolved in anhydrous acetonitrile (80 ml). Anhydrous potassium carbonate (1.67 g, 12 mmol) was added and the mixture was stirred 4 hours at 55-60° C. Reaction mixture was allowed to cool down to RT and filtrated through elite pad. The filtrate was evaporated to dryness and the product was purified with column chromatography using silica as a stationary phase and dichloromethene:methanol (5% 95:5) as an eluent. Yield: 1.57 g (71%) 1HNMR (CDCl3, δ ppm): 8.12 (2H, d, J=1.60 Hz), 8.07 (2H, d, J=1.40 Hz), 7.76 (2H, s), 4.46 (4H, q, J=7.12 Hz), 4.18 (4H, q, J=7.13), 4.08 (4H, s), 3.92 (4H, s), 3.49 (4H, s), 1.42 (6H, t, J=7.13), 1.28 (6H, t, J=7.13). MS(ESI-TOF) calculated for C33H38Br2IN5O8 [M+H]+: 918.02, found: 917.92

Example 8

Synthesis of diethyl 6,6'-((((4-((4-aminophenyp-ethynyl)pyridine-2,6-diyl)bis(methylene))bis((2-ethoxy-2-oxoethyl)azanediyl))bis(methylene))bis(4-bromopicolinate) (11)

Compound 10 (412 mg, 0.45mmol) was dissolved in anhydrous dichloromethane (6 ml), Triethylarnine (2 ml), copper (I) iodide (3.2 mg, 0.017 mmol), bis(triphenylphosphine)palladium(II) dichloride (9.5 mg, 0.014 mmol) and 4-ethynyianiline (52.5 mg, 0.45 mmol) were added, The reaction mixture was de-aerated with argon and the mixture was stirred 3 h at RT. Reaction mixture was evaporated to dryness and the product was purified with column chromatography using silica as a stationary phase and dichloromethane:methanol (10% 90:10) as an eluent. Yield 193 mg (47%) 1HNMR: (CDCl3, δ ppm): 8.11 (2H, d, J=1.35 Hz), 7.83 (2H, s), 7.32 (2H, d, J=8.15 Hz), 7.18 (2H, s), 6.67 (2H, d, J=8.45 Hz), 4.38 (4H, s), 4.30 (4H, q, J=6.74 Hz), 4.01 (4H, q, J=7.10 Hz), 3.97 (4H, s), 3.39 (4H, s), 1.32 (6H, t, J=6.90 Hz), 1.17 (6H, t, J=6.93 Hz), MS(ESI-TOF) calculated for C41H44Br2N6O8 [M+H]+: 907.17, found: 907.05

Example 9

Synthesis of tetraethyl 2,2',2'',2'''-((((6,6'-((((4-((4-aminophenyl)ethynyl)pyridine-2,6-diyl)bis(methylene))bis((2-ethoxy-2-oxoethyl)azanediyl))bis(methylene))bis(2-(ethoxycarbonyl)pyridine-6,4-diyl))bis(ethyne -2,1-diyl))bis(benzene-4,2,1-triyl))tetrakis(oxy))tetraacetate) (12)

Compounds 4 (0,162 g, 0.529 mmol) and 11 (0.200 g, 0.221 mmol) were dissolved to a mixture of anhydrous tetrahydrofuran (2.5 ml) and triethylamine (2.5 ml). Bis(triphenylphosphine)palladium(II) dichloride (6.2 mg, 0.009 mmol) and copper (I) iodide (3.4 mg, 0.018 mmol) were added and the mixture was stirred overnight under argon atmosphere at 55° C. The mixture was filtered and concentrated. The product was purified by column chromatography using silica gel as the stationary phase and 10% ethanol:dichloromethane as eluent. Yield: 86.4 mg (29%) MS(ESI-TOF) calculated for $C_{73}H_{78}N_6O_{20}$ [M+] 1358.53, Found: 1358.48

Example 10

Synthesis of 6.6'-((((4-((4-aminophenyl)ethynyl)pyridine-2,6-diyl)bis(methylene))bis((carboxylatomethyl)azanediyl))bis(methylene))bis(4-((2,4-bis(carboxymethoxy)phenyl)ethynyl)picolinate europium (III) (13)

Compound 12 (84.1 mg, 0.0619 mmol) was dissolved in the mixture of water (2.5 ml) and 0.5M potassium hydroxide solution in ethanol (4.2 ml), Mixture was stirred at RT for 2 h. Reaction mixture was evaporated to dryness, the residue was dissolved in water (2 ml) and pH was adjusted to 6.7 by addition of hydrochloric acid (6M). Europium chloride (22.7 mg, 0.0619 mmol) dissolved in water (0.5 ml) was added to the reaction mixture drop-wise. Reaction mixture was stirred at RT for 1 h 15 min and the pH was maintained at 6.3-6.5 by addition of sodium hydrogen carbonate to the mixture. Excess of europium was precipitated from the mixture by adjusting pH to 8.5-9.0 by addition of sodium hydroxide and the precipitate was removed by centrifugation. The product was precipitated from the supernatant with acetone and isolated by centrifugation. The precipitate was washed with acetone (3×10 ml) and the product was dried overnight in vacuum desiccator over silica gel. Yield: 199.4 mg MS(ESI-TOF) calculated for $C_{57}H_{42}EuN_6O_{20}$— $[M-H]^{2-}$ 641.09, found: 641.16.

Example 11

Synthesis of 6,6'-((((4-((4-isothiocyanatophenyl)ethynyl)pyridine-2,6-diyl)bis(methylene))bis((carboxylatomethyl)azanediyl))bis(methylene))bis(4-((2,4-bis(carboxymethoxy)phenyl)ethynyl)picolinate) europium(III) (14)

Aqueous solution of compound 13 (90.5 mg, 0.0708 mmol) was added drop-wise in 15 minutes to a mixture of chloroform (1.5 ml), thiophosgen (35.8 µl, 0.469 mmol) and sodium hydrogen carbonate (44.4 mg, 0.591 mmol). The two phases were separated and the aqueous phase was washed with chloroform (3×6 ml). The product was precipitated from the aqueous phase with acetone (60 ml) and isolated by centrifugation, The precipitate was washed with acetone (3×10 ml) and dried overnight in vacuum desiccator over silica gel. Yield: 85.0 mg MS(ESI-TOF) calculated for $C_{58}H_{40}EuN_6O_{20}S$— $[M-H]^{2-}$ 662.06, found: 662.16.

Example 12

Synthesis of diethyl 2,2'-(((4-bromo-6-(bromomethyl)pyridin-2-yl)methyl)azanediyl)diacetate (16)

Compound 15 (9.79 g, 28.5 mmol, Acta Chem. Scand B 42, 1988, 373) was dissolved in acetonitrile (196 ml, dry). Diethyl iminodiacetate (2.55 ml, 14.2 mmol) was added and the mixture was stirred at 60-65° C. for 2 h 30 min. The mixture was evaporated to dryness and purified by column chromatography using silica gel as the stationary phase and 20% ethyl acetate:petroleum ether as eluent. Yield: 3.36 g (52%) $^1$H NMR (CDCl$_3$, δ ppm): 7.80 (1H, d, J=1.5 Hz), 7.51 (1H, d, J=1.5 Hz), 4.47 (2H, s), 4.18 (4H, m), 4.05 (2H, s), 3.62 (4H, s) 1.28 (6H, m).

Example 13

Synthesis of tetraethyl 2,2',2",2"'-(((6,6'-(((4-aminophenethyl)azanediyl)bis(methylene))bis(4-bromopyridine-6,2-diyl))bis(methylene))bis(azanetriyl)) tetraacetate (17)

Compound 16 (3.30 g, 7.29 mmol) was dissolved in acetonitrile (66 ml, dry). Potassium carbonate (5.04 g, 36.5 mmol, dry) and 2-(4-Aminophenyl)ethylamine (0.50 g, 3.68 mmol) were added and the mixture was stirred at 50-55° C. for 4 h. The mixture was filtered through celite and the precipitate was washed with acetonitrile. The filtrate was evaporated to dryness and then purified by column chromatography using silica gel as the stationary phase and triethylamine:ethyl acetate:petroleum ether (1:2:7) as eluent. Yield 2.02 g (63%) $^1$H NMR (CDCl$_3$, δ ppm): 7.69 (2H, d, J=1.6 Hz), 7.42 (2H, d, 1.6 Hz), 6.90 (2H, d, J=8.35 Hz), 6.62 (2H, d, J=8.35), 4.14 (8H, m), 4.01 (4H, s) 3.79 (4H, s), 3.60 (8H, s), 2.73 (4H, m), 1.27 (12H, t, J=7.15 Hz).

Example 14

Synthesis of tetraethyl 2,2',2",2"'-(((6,6'-(((4-aminophenethyl)azanediyl)bis(methylene))bis(4-((2,4-bis (2-ethoxy-2-oxoethoxy)phenyl)ethynyl)pyridine-6,2-diyl))bis(methylene))bis(azanetriyl))tetraacetate (18)

Compound 4 (0.174 g, 0.568 mmol) and compound 17 (0.315 g, 0.358 mmol) were dissolved to a mixture of anhydrous tetrahydrofuran (4.0 ml) and triethylamine (4.0 ml). Bis(triphenylphosphine)palladium(II) dichloride (6.6 mg, 0.009 mmol) and copper (I) iodide (3.6 mg, 0.019 mmol) were added and the mixture was stirred overnight under argon atmosphere at 55° C. The mixture was filtered and concentrated. The product was purified by column chromatography using silica gel as the stationary phase and triethylamine:ethyl acetate:petroleum ether (2:3:5) as eluent. Yield 104.7 mg (22%) $^1$H NMR (CDCl$_3$, δ ppm): 7.52 (2H, s), 7.44 (2H, s), 7.41 (2H, d, J=9.1 Hz), 6.89 (2H, d, 8.3 Hz), 6.58 (2H, d, J=8.3 Hz), 6.40 (4H, m), 4.69 (4H, s), 4.59 (4H, s), 4.30-4.13 (16H, m), 4.04 (4H, s), 3.86 (4H, s), 3.61 (8H, s), 2.76 (4H, m), 1.32-1.23 (24H, m).

Example 15

Synthesis of 2,2',2",2"'-(((6,6'-(((4-aminophenethyl) azanediyl)bis-(methylene))bis(4-((2,4-bis(carboxymethoxy)phenyl)ethynyl)pyridine-6,2-diyl))bis -(methylene))bis(azanetriyl))tetraacetate europium (III) (19)

Compound 18 (101.2 mg, 0.076 mmol) was dissolved in the mixture of water (3.3 ml) and 0.5M potassium hydroxide solution in ethanol (5.1 ml). Mixture was stirred at RT for 2 h. Reaction mixture was evaporated to dryness and the residue was dissolved in water (1.7 ml). The solution was stirred for 30 min and the pH was adjusted to 6.7 by addition of hydrochloric acid (6M). Europium chloride (27.9 mg, 0.076 mmol) dissolved in water (0.6 ml) was added to the reaction mixture drop-wise. Reaction mixture was stirred at RT for 45 min and the pH was maintained at 6.3-6.7 by addition of sodium hydrogen carbonate to the mixture. Excess of europium was precipitated from the mixture by adjusting pH to 8.5-9.0 by addition of sodium hydroxide and the precipitate was removed by centrifugation. The product was precipitated from the supernatant with acetone and isolated by centrifugation. The precipitate was washed with acetone (3×10 ml) and the product was dried overnight in a vacuum desiccator over silica gel. Yield: 279.4 mg. MS(ESI-TOF) calculated for $C_{54}H_{48}EuN_6O_{20}$— [M–H]$^{2-}$ 626.10, found: 626.16.

Example 16

Synthesis of 2,2',2",2"'-(((6,6'-(((4-isothiocyanatophenethyl)azanediyl)-bis(methylene))bis(4-((2,4-bis (carboxymethoxy)phenyl)ethynyl)pyridine-6,2-diyl)) bis -(methylene))bis(azanetriyl))tetraacetate europium(III) (20)

Aqueous solution of compound 19 (99.6 mg, 0.0797 mmol) was added drop-wise in 10 minutes to a mixture of chloroform (1.6 ml), thiophosgen (40.4 μl, 0.530 mmol) and sodium hydrogen carbonate (50.2 mg, 0.597 mmol). Mixture was stirred at RT for 20 min. Phases were separated and the aqueous phase was washed with chloroform (4×2 ml). Product was precipitated from the aqueous phase with acetone (60 ml) and isolated by centrifugation. The precipitate was washed with acetone (3×30 ml) and dried overnight in a vacuum desiccator over silica gel. Yield: 116.2 mg. MS(ESI-TOF) calculated for $C_{55}H_{46}EuN_6O_{20}S$— [M–H]$^{2-}$ 647.08, found: 647.15.

Example 17

Synthesis of triethyl 2,2',2"-((4-iodo-1,3,5-phenylene)tris(oxy))triacetate (21)

A mixture of 4-Iode-1,3,5-trihydroxybenzene (3.41 g, 13.5 mmol; Acta Chem. Scand. 1991, 45, 539), dry K$_2$CO$_3$ (6.17 g, 44.7 mmol), ethyl bromoacetate (4.96 ml, 44.7 mmol) and dry MeCN (100 ml) was stirred overnight at 55° C. The mixture was filtered, the solid material washed with MeCN and the filtrate was evaporated to dryness. The product was purified by column chromatography using silica gel as stationary phase and MeOH:CH$_2$Cl$_2$ (first 0:100, then 20:80) as eluent. Yield: 0.64 g (9%) $^1$H NMR (CDCl$_3$, δ ppm): 6.10 (2H, s), 4.65 (4H, s), 4.55 (4H, s), 4.27 (2H, q, J=7.15 Hz), 4.26 (4H, q, J=7.15 Hz), 1.31 (3H, t, J=7.15 Hz), 1.30 (6H, t, J=7.15 Hz). MS(ESI-TOF) calculated for $C_{18}H_{23}IO_9$ [M+H]$^{3o}$ : 511.05, found: 510.93.

Example 18

Synthesis of triethyl 2,2',2"-((4-(trimethylsilyl)ethynyl-1,3,5-phenylene)tris(oxy))-triacetate (22)

Compound 22 was synthesized from the compound 21 using a method analogous to the synthesis described in the Example 2. The mixture was stirred first at 100° C. for 30 minutes, then at 120° C. for 20 minutes by using microwave heating. The mixture was extracted with Et$_2$O (50 ml), washed with H$_2$O (2×20 ml), dried with Na$_2$SO$_4$, and the product purified by column chromatography using silica gel as stationary phase and ethyl acetate:petroleum ether (first 20:80, then 30:70) as eluent. Yield: 70% $^1$H NMR (CDCl$_3$, δ ppm): 6.10 (2H, s), 4.67 (4H, s), 4.55 (2H, s), 4.27 (2H, q, J=7.15 Hz), 4.26 (4H, q, J=7.15 Hz), 1.30 (6H, t, J=7.15 Hz), 1.29 (3H, t, J=7.15 Hz). 0.26 (9H, s). MS(ESI-TOF) calculated for C$_{23}$H$_{32}$O$_9$Si [M+H]$^{30}$ : 481.19, found: 481.99.

Example 19

Synthesis of triethyl 2,2',2"-((4-ethynyl-1,3,5-phenylene)tris(oxy))triacetate (23)

This compound 23 was synthesized from the compound 22 using a method analogous to the synthesis described in the Example 3. After washings with 10% citric acid and H$_2$O, the product (100%) was used for the next step without further purifications. $^1$H NMR (CDCl$_3$, δ ppm): 6.06 (2H, s), 4.69 (4H, s), 4.55 (2H, s), 4.27 (2H, q, J=7.15 Hz), 4.26 (4H, q, J=7.15 Hz), 3.50 (1H, s), 1.30 (3H, t, J=7.15 Hz), 1.29 (6H, t, J=7.15 Hz). 0.26 (9H, s). MS(ESI-TOF) calculated for C$_{20}$H$_{24}$O$_9$ [M+H]$^{30}$ : 409.15, found: 409.20.

Example 20

Synthesis of N-(4-ethynylphenyl)-2,2,2-trifluoroacetamide (24)

4-Ethynylaniline (1.38 g, 11.8 mmol) was added in small portions into an ice-cold (CF$_3$CO)$_2$O (6.6 ml). After stirring for 10 min in ice-bath, the mixture was stirred for 2.5 hours at room temperature. The mixture was poured into ice-H$_2$O (100 ml), the product filtered and washed with H$_2$O. The product (2.29 g, 91%) was used for the next step without further purifications. $^1$H NMR (CDCl3): δ (ppm)) 8.08 (1H, s), 7.55 (2H, d, J=8.80 Hz), 7.51 (2H, d, J=8.80 Hz), 3.1 (1H, s). MS(ESI-TOF) calculated for C$_{10}$H$_6$F$_3$NO [M+H]$^{30}$ : calculated 214.02, found 213.07.

Example 21

Synthesis of N-(4-((2,6-bis(hydroxymethyl)pyridin-4-yl)ethynyl)phenyl)-2,2,2-trifluoroacetamide (25)

A mixture of the compound 24 (0.55 g, 2.58 mmol) and 6-bromo-2,6-dihydroxyrnethylpyridine (0.47 g, 2.15 mmol; Acta Chem. Scand. 1988, Ser B, 42, 614) in dry triethylamine (5 ml) and tetrahydrofurane (10 ml) was de-aerated with argon. After addition of bis(triphenylphosphine)-palladium(II) chloride (30 mg, 43 μmol) and CuI (16 mg, 86 μmol), the mixture was stirred for 19 hours at 55° C. After evaporation to dryness, the residue was treated with a cold mixture of CH$_2$Cl$_2$ (40 ml) and H$_2$O (20 ml), filtered and the product (0.56 g, 75%) washed with cold H$_2$O (10 ml) and CH$_2$Cl$_2$(10 ml). Yield: 0.56 g (75%). $^1$H NMR (D6-DMSO, δ ppm): 11.4 (1H, bs), 7.79 (2H, d, J=8.80 Hz), 7.68 (2H, d, J=8.80 Hz), 7.42 (2H, s), 5.49 (2H, bs), 4.56 (4H, s). MS(ESI-TOF) calculated for C$_{17}$H$_{13}$F$_3$N$_2$O$_3$ [M+H]$^{30}$ : calculated 351.10, found 351.96.

Example 22

Synthesis of N-(4-((2,6-bis(bromomethyl)pyridin-4-yl)ethynyl)phenyl)-2,2,2-trifluoroacetamide (26)

PBr$_3$ (225 μl) was added in a suspension of the compound 24 (0.56 g, 1.6 mmol) in CHCl$_3$ (65 ml). After stirring for 20 hours at 60° C., the mixture was neutralized with 5% NaHCO$_3$ (35 ml). The aqueous phase was extracted with CHCl$_3$ (40 ml) and the combined organic phases were dried with Na$_2$SO$_4$, filtered and evaporated to dryness. The product 25 (1.09 g, 93%) was used for the next step without further purifications. $^1$H NMR (CDCl$_3$, δ ppm): 7.93 (1H, s), 7.63 (2H, d, J=8.68 Hz), 7.59 (2H, J=8.68 Hz), 7.47 (2H, s), 4.53 (4H, s). MS(ESI-TOF) calculated for C$_{17}$H$_{11}$Br$_2$F$_3$N$_2$O [M+H]$^{30}$ : calculated 474.93, 476.93, 498.92, found 475.38, 477.44, 479.45.

Example 23

Synthesis of diethyl 6,6'-(((((4-((4-trifluoroacetamidophenyl)ethynyl)-pyridine-2,6-diyl)bis(methylene)) bis((2-ethoxy-2-oxoethyl)azanediyl))bis(methylene))-bis(4-bromopicolinate) (27)

This compound 27 was synthesized from the compounds 26 and 9 using a method analogous to the synthesis described in the Example 7. Reaction time at 70° C. was 27 hours. The product was purified by column chromatography using silica gel as stationary phase and triethylamine:ethyl acetate:petroleum ether (1:69:30) as eluent. Yield: 66%. $^1$H NMR (CDCl$_3$, δ ppm): 8.53 (1H, s), 8.14 (2H, d, J=1.80 Hz), 8.11 (2H, d, J=1.80 Hz), 7.68 (2H, d, J=8.73 Hz), 7.60 (2H, d, J=8.73 Hz), 7.34 (2H, s), 4.44 (4H, q, J=7.08 Hz), 4.18 (4H, q, J=7.15 Hz); 4.10 (4H, s), 3.98 (4H, s), 3.50 (4H, s), 1.40 (6H, t, J=7.08 Hz), 1.28 (6H, t, J=7.15 Hz). MS(ESI-TOF) calculated for C$_{43}$H$_{43}$Br$_2$F$_3$N$_6$O$_9$ [M+H]$^{30}$ : calculated 1003.15, 1005.15, 1007.15, found 1003.71, 1005.48, 1007.58.

Example 24

Synthesis of the compound 28

A mixture of the compound 27 (120 g, 0.148 mmol) and 23 (145 mg, 0.355 mmol) in dry triethylamine (1 ml) and tetrahydrofurane (2 ml) was de-aerated with argon, After addition of bis(triphenylphosphine)palladium(II) chloride (10 mg, 14 μmol) and CuI (6 mg, 28 μmol), the mixture was stirred for 22 hours at 55° C. After evaporation to dryness, the residue was dissolved in CH$_2$Cl$_2$ (40 ml), washed with H$_2$O (3×10 ml) and dried with Na$_2$SO$_4$. The product was purified by column chromatography using silica gel as stationary phase and triethylamine:ethyl acetate:petroleum ether (1:69:30) as eluent. Yield: 115 mg 47%. $^1$H NMR (CDCl$_3$, δ ppm): 9.12 (1H, s), 8.09 (2H, d, J=1.25 Hz), 8.06 (2H, d, J=1.25 Hz), 7.57 (2H, s), 7.34 (2H, d, J=8.80 Hz), 7.30 (2H, d, J=8.80 Hz), 5.97 (4H, s), 4.63 (8H, s), 4.60 (4H, s), 4.45 (4H, q, J=7.12 Hz), 4.30 (4H, q, J=7.12 Hz), 4.21 (8H, q, J=7.12 Hz), 4.17 (4H, q, J=7.12 Hz), 4.10 (4H, s), 4.02 (4H, s), 3.52 (4H, s), 1.42 (6H, t, J=7.12 Hz), 1.33 (6H, t, J=7.12 Hz), 1.29 (6H, J=7.12 Hz), 1.25 (12H, t, J=7.12 Hz). MS(ESI-TOF) calculated for C$_{83}$H$_{89}$F$_3$N$_6$O$_{27}$ [M+H]$^{30}$ : calculated 1659.58, found 1659.81.

Example 25

Synthesis of the Europium(III) Chelate 29

A mixture of the compound 28 (105 mg, 63 μmol) and 0.5M KOH in ethanol (9 ml) was stirred for 30 minutes at room temperature and water was added (2 ml). After stirring for 3 hours at room temperature, EtOH was evaporated, the residue was stirred for 30 minutes at room temperature, and the pH was adjusted to ca. 6.5 with 6M HCl. Europium(III) chloride (23 mg, 63 μmol) in H$_2$O (0.17 ml) was added within 10 minutes and the pH was maintained at 5-7 with solid NaHCO$_3$. After stirring for overnight at room temperature, the pH was raised to 8.5 with 1M NaOH, the precipitate was centrifuged off and the supernatant was extracted with phenol (once with 0.75 g and 3×0.5 g). The combined phenol phases were treated with H$_2$O (1 ml) and Et$_2$O (20 ml), the aqueous phase was washed with Et$_2$O (2×20 ml), and triturated with acetone. The precipitate was centrifuged and washed with acetone. The product was used for the next step without further purification. Conditions for HPLC run: Reversed phase HPLC (RP-18 column). The solvents were A: Triethyl ammonium acetate buffer (20 mM, pH7) and B: 50% acetonitrile in triethyl ammonium acetate buffer (20 mM, pH7). The gradient was started from 5% of solvent B and the amount of solvent B was linearly raised to 100% in 25 minutes. R$_f$(HPLC)=14.5 min. UV/VIS=359 nm.

Example 26

Synthesis of the Europium(III) Labeling Chelate 30

This compound 30 was synthesized from the chelate 29 using a method analogous to the synthesis described in the Example 11. Conditions for HPLC run: see example 35. R$_f$(HPLC)=20.9 min. UV/VIS=325 (sh), 340 and 362 (sh) nm.

Example 27

Synthesis of the Europium(III) Chelate 31

This compound 31 was synthesized from the chelate 30 using a method analogous to the synthesis described in the Example 38, R$_f$(HPLC)=14.3 min. UV/VIS=349 nm.

Example 28

Synthesis of 1-Bromo-3,5-dihydroxybenzene (33)

1-bromo-3 5-dimethoxybenzene (32) (1.00 g, 4.60 mmol) was dissolved in dry dichloromethane (40 ml) and cooled in an ice bath. Boron tribromide (1.33 ml, 13.82 mmol) was added and the mixture was stirred on 2 h. The mixture was allowed to warm up to room temperature and stirred overnight. Methanol (1.4 ml) was added drop-wise to terminate the reaction, and the mixture was poured into water (50 ml) and stirred at RT for 2 h. Reaction mixture was neutralized with NaHCO$_3$ and the mixture extracted twice with ethyl acetate (30 ml). Combined organic layers were dried over Na$_2$SO$_4$ and evaporated to dryness. Product was purified by column chromatography using silica gel as stationary phase and methanol:dichloromethane (5:95) as eluent. Product was a white solid. Yield: 0.71 g (81%). $^1$HNMR (DMSO-d6, δ ppm): 9.68 (2H, s), 6.38 (2H, d, J=2 Hz), 6.19 (1H, dd, J=2 Hz).

Example 29

Synthesis of di-tert-butyl 2,2'-((5-bromo-1,3-phenylene)bis(oxy))diacetate (34)

Compound 33 (0.49 g, 2.59 mmol) was dissolved in DMF (10 ml, dry). Anhydrous K$_2$CO$_3$ (2.15 g, 15.56 mmol) and tert-butyl bromoacetate (1.15 ml, 7.78 mmol) were added and the mixture was stirred overnight under argon atmosphere at 50° C. Water (17 ml) was added and the mixture was extracted with ethyl acetate (3×40 ml). Combined organic extracts were dried over NaHCO$_3$ and evaporated to dryness. Crude product was purified by column chromatography using silica gel as stationary phase and dichloromethane as eluent. Product was a white solid. Yield: 0.95 g (87%) $^1$HNMR (CDCl$_3$, δ ppm): 6.67 (2H, d, J=2 Hz), 6.42 (1H, dd, J=2 Hz), 1.49 (18H, s)

Example 30

Synthesis of di-tert-butyl 2-2'-((5-((trimethylsilyl)ethynyl)-1,3-phenylene)bis(oxy))diacetate (35)

Compound 34 (2.00 g, 4.79 mmol) was dissolved in DMF (4 ml, dry) and the solution was placed in a microwave reaction vial. Diethyl amine (12 ml, dry), Pd(PPh$_3$)$_2$Cl$_2$ (168 mg, 0.24 mmol), CuI (46 mg, 0.24 mmol) and PPh$_3$ (251 mg, 0.96 mmol) were added and the vial was sealed in an argon atmosphere. Trimethylsilyl acetylene (996 μl, 7.19 mmol) was added through a septum and the mixture was stirred at 120° C. for 30 minutes using microwave heating. Reaction mixture was evaporated to dryness, dissolved in dichloromethane and purified by column chromatography using silica gel as stationary phase and ethyl acetate:petroleum ether (10:90) as eluent. Yield: 1.36 g (65%) $^1$H NMR (CDCl$_3$, δ ppm): 6.61 (2H, d, J=2.35 Hz), 6.49 (1H, dd, J=2.3 Hz), 4.46 (4H, s), 1.49 (18H, s), 0.23 (9H, m).

Example 31

Synthesis of di-tert-butyl 2,2'-((5-ethynyl-1,3-phenylene)bis(oxy))diacetate (36)

Compound 35 (1.29 g, 2.98 mmol) was dissolved in dichloromethane (40 ml, dry). Tetrabutyl ammonium fluoride (0.934 g, 3.57 mmol) was added and the mixture was stirred in argon atmosphere at room temperature for 45 min. Mixture was washed with 10% citric acid solution (20 ml), and four times with water (4×40 ml). The organic phase was dried over Na$_2$SO$_4$ and evaporated to dryness. Crude product was purified by column chromatography using silica gel as stationary phase and ethyl acetate:petroleum ether (10:90) as eluent. Product was a yellowish solid. Yield: 895 mg (83%). $^1$H NMR (CDCl$_3$, δ ppm): 6.64 (2H, d, J=2.3 Hz), 6.51 (1H, dd, J=2.33 Hz), 4.47 (4H, s), 3.02 (1H, s), 1.49 (18H, s).

Example 32

Synthesis of tetra-tert-butyl 2,2',2'',2'''-(((((6,6'-((((4-((4-aminophenyl)ethynyl)pyridine-2,6-diyl)bis(methylene))bis((2-ethoxy-2-oxoethyl)azanediyl))bis(methylene))bis(2-(ethoxycarbonyl)pyridine-6,4-diyl))bis(ethyne -2,1-diyl))bis(benzene-5,3,1-triyl))tetrakis(oxy))tetraacetate (37)

Compound 36 (0.167 g, 0,459 mmol) and compound 11 (0,167 g, 0.184 mmol) were dissolved in mixture of anhydrous tetrahydrofurane (4 ml) and triethyiamine (2.5 ml). Bis(triphenylphosphine)palladium(II) dichloride (3.8 mg, 0.0054 mmol) and copper (I) iodide (2.3 mg, 0.012 mmol) were added and the mixture was stirred overnight under argon atmosphere at 55-60° C. Reaction mixture was evaporated to dryness and purified by column chromatography using silica gel as stationary phase and methanol:dichloromethane (10:90) as eluent. Yield: 71 mg (27%) MS(ESI-TOF) calculated for C$_{81}$H$_{94}$N$_6$O$_{20}$ [M+H]$^+$: 1471.66, Found: 1471.68

Example 33

Synthesis of 6,6'-(((((4-((4-aminophenypethynyp-pyridine-2,6-diyl)bis(methylene))bis((carboxylatomethyl)azanediyl))bis(methylene))bis(4-((3,5-bis(carboxymethoxy)phenyl)ethynyl)picolinate europlum (III) (38)

Compound 37 (68 mg, 0.048 mmol) was dissolved in trifluoroacetic add (1 ml, 13.5 mmol) and the mixture was stirred at RT for 1.5 h. Reaction mixture was evaporated to dryness without heating. Diethyl ether (2.5 ml) was added to the residue and the mixture was stirred for 15 minutes. Product precipitated from the mixture and was isolated by centrifugation. The precipitate was washed twice with diethyl ether and then dried in vacuum desiccator over silica gel. Dried precipitate (64 mg, 0.051 mmol) was dissolved in the mixture of water (1.8 ml) and 0.5M potassium hydroxide solution in ethanol (4 ml). Mixture was stirred in RT for 2 h. Reaction mixture was evaporated to dryness and the residue was dissolved in water (1.7 ml). pH was adjusted to 6.5 by addition of hydrochloric acid (6M). Europium chloride (20 mg, 0.055 mmol) dissolved in water (485 µl) was added to the reaction mixture drop-wise. Reaction mixture was stirred at RT for 2 hours and the pH was maintained at 6.3-6.5 by addition of sodium hydrogen carbonate to the mixture. Excess of europium was precipitated from the mixture by adjusting pH to 8.5-9.0 by addition of sodium hydroxide and the precipitate was removed by centrifugation. The product was precipitated with acetone (25 ml) and isolated by centrifugation. The precipitate was washed with acetone (3×10 ml) and dried overnight in vacuum desiccator over silica gel. Yield: 180 mg. MS(ESI-TOF) calculated for $C_{57}H_{42}EuN_6O_{20}$ $[M+2H]^+$: 1285.18, Found: 1285.24

Example 34

Synthesis of 6,6'(((((4-((4-isothiocyanatophenyl)ethynyl)pyridine-2,6-diyl)bis(methylene))bis((carboxylatomethyl)azanediyl))bis(methylene))bis(4-((3,5-bis(carboxymethoxy)phenyl)ethynyl)picolinate) europium(III) (39)

Aqueous solution of compound 18 (175 mg, 0.143 mmol) was added drop-wise to a mixture of chloroform (2.85 ml), thiophosgene (74 µl, 0.97 mmol) and sodium hydrogen carbonate (91 mg, 1.09 mmol). Reaction mixture was stirred at RT for 45 min. The two phases were separated and the aqueous phase was washed with chloroform (3×6 ml). pH was adjusted to 7 with 1M acetic acid and the product was precipitated with acetone (57 ml) and isolated by centrifugation. The precipitate was washed with acetone (3×15 ml) and dried overnight in vacuum desiccator over silica gel. Yield: 216 mg. MS(ESI-TOF) calculated for $C_{58}H_{40}EuN_6O_{20}S$— $[M-H]^{2-}$ (for free acids without sodium ions): 662.56, Found: 662.47.

Example 35

Synthesis of tetra(tertbutyl) 2,2',2", 2'"-(((6,6'-(((4-aminophenethyl)azanediyl)bis(methylene))bis(4-((3,5-bis(2-ethoxy-2-oxoethoxy)phenyl)ethynyl)pyridine-6,2-diyl))bis(methylene))bis(azanetriyl)) tetraacetate (40)

Compound 40 was prepared from compounds 36 (0.88 g, 2.44 mmol) and tetra(tert-butyl) 2,2',2",2'"-(((6,6'-(((4-aminophenethyl)azanediyl)bis(methylene))bis(4-bromopyridine-6,2-diyl))bis(methylene))bis(azanetriyl))tetraacetate (1.01 g, 1.02 mmol) (prepared according to von Lode P. et al., Anal. Chem., 2003, 75, 3193-3201) using a method analogous to the synthesis described in the Example 14. MS(MALDI) calculated for $C_{86}H_{116}N_6O_{20}$ $[M+H]^+$: 1554.82, Found: 1554.71.

Example 36

Synthesis of 2,2',2"2'"-(((6,6- 4-aminophenethyl)azanediyl)bis-(methylene))bis(4-((3,5-bis(carboxymethoxy)phenyl)ethynyl)pyridine-6,2-diyl))bis -(methylene))bis(azanetriyl))tetraacetate europium (III) (41)

Compound 40 (0.87 g, 0.56 mmol) was dissolved in trifluoroacetic acid (20 ml, 250 mmol) and the mixture was stirred in RT for 2 h. Reaction mixture was evaporated to dryness without heating. Diethyl ether (30 ml) was added to the residue and the mixture was stirred for 15 minutes. Precipitated product was isolated by centrifugation. The precipitate was washed with diethyl ether and then dried in vacuum desiccator over silica gel. Dried precipitate (0.30 g) was dissolved in water (6 ml). pH was adjusted to 6.5 by addition of sodium hydroxide and hydrochloric acid, Europium chloride (0.10 mg, 0.27 mmol) in water (2 ml) was added to the reaction mixture drop-wise. pH was maintained at 6,3-6,5 by addition of solid sodium hydrogen carbonate to the mixture. Reaction mixture was stirred at RT for 30 minutes. pH was adjusted to 8.5-9.0 by addition of sodium hydroxide. The product was precipitated with acetone and isolated by centrifugation. The product was dried overnight in vacuum desiccator over silica gel. MS(ESI-TOF) calculated for C54H48EuN6O20- $[M+3H]2+$: 628.01, Found: 628.12. HPLC retention time 15.38 minutes (buffers and conditions same as in example 35). UV-maximum 304 nm.

Example 37

Synthesis of 2,2',2",2'"-(((6,6'-(((4-isothiocyanatophenethyl)azanediyl)-bis(methylene))bis(4-((3,5-bis (carboxymethoxy)phenyl)ethynyl)pyridine-6,2-diyl)) bis -(methylene))bis(azanetriyl))tetraacetate europium(III) (42)

Compound 42 was prepared from 41 using a method analogous to the synthesis described in the Example 16. MS(ESI-TOF) calculated for C55H46EuN6O20S-[M+H]: 1294.17, Found: 1294.72. HPLC retention time 17.42 minutes (buffers and conditions same as in Example 38). UV-maximum 302 nm.

Example 38

Preparation of Taurine Derivative 43, 44 and 46

Compound 14 (10.0 mg), compound 20 (10.0 mg) and conventional 9-dentate α-galactose Eu chelate (46) (prepared according to von Lode P. et al., Anal. Chem., 2003, 75, 3193-3201) (5.5 mg) respectively were coupled to taurine (5 mg for each reaction) by dissolving the starting materials in aqueous sodium hydrogen carbonate (2 ml, 50 mM, pH9.8). The mixtures were incubated overnight at RT. The products (43, 44 and 46) were purified by using reversed phase HPLC (RP-18 column). The solvents were A: Triethyl ammonium acetate buffer (20 mM, pH7) and B: 50% acetonitrile in triethyl ammonium acetate buffer (20 mM, pH7). The gradient was started from 5% of solvent B and the amount of solvent B was linearly raised to 100% in 30 minutes except for 46, for which it was raised to 100% in 25 minutes. The products eluted from the column at 16.9 min (43), 15.1 (44) and at 15.1 min (46) time points. Fractions containing the products were collected, pooled and evaporated to dryness. The other two taurine derivatives 47 and 48 were prepared from corresponding chelates 39 and 42, respectively, using the same method described above. The products eluted from the column at 16.6 min (47) and at 14.5 min (48) time points.

Example 39

Excitation Spectrum of Compound 20

The excitation spectrum of the prepared chelate 20 was measured both in liquid phase and in dry state. For comparison also an excitation spectrum of the reference compound (45) is presented in FIG. 1. (liquid phase measurement, dashed line). The excitation spectrum shows a dear red-shift compared to the reference compound in the excitation maximum thus allowing efficient excitation also with longer wavelength for example excitation with 365 nm LED.

Example 40

Comparison between luminescence of taurine derivatives of Eu-chelates according to present disclosure (43 (taurine of compound 14) and 44 (taurine of compound 20) and a conventional 9-dentate α-galactose Eu chelate (46 (taurine of compound 45))

The purified taurine derivative were dissolved in water and analyzed for UV spectrum, Eu-content with DELFIA® against Eu standard material and luminescence signal in TSA buffer for 43 and 44, and in water for 46 with Victor™ Plate fluorometer. Luminescence yields were calculated using the luminescence measurement data and luminescence yield reported by von Lode P. at al., *Anal. Chem.*, 2003, 75, 3193-3201. The results are summarized in Table 1.

TABLE 1

|  | Compound 46 (reference compound) | Compound 43 | Compound 44 |
| --- | --- | --- | --- |
| Molar absorptivity ($\epsilon$) based on Eu content | 56,000 | 85,000 | 59,000 |
| Luminescence yield ($\epsilon\phi$) | 4,800 | 14,900 | 5,500 |

Example 41

Comparison between luminescence properties of Eu-chelates (43 and 44) according to the present disclosure and conventional chelates 47 and 48, respectively. The measured photo-physical properties excitation wavelengths ($\lambda_{exc}$), luminescence decay times ($\tau$), molar absorptivities ($\epsilon$), estimated luminescence yields ($\epsilon\phi$) of the novel chelates 43 and 44 compared to the conventional chelates 47 and 48, respectively, in 50 mM TRS buffer (pH 7.75) are in the Table 2 and 3.

TABLE 2

| Chelate | $\epsilon$ | $\epsilon\phi$ | $\phi$ | Mean lifetime (ms) | Excitation max. (nm) |
| --- | --- | --- | --- | --- | --- |
| 47 | 83000 | 14100 | 0.17 | 0.93 | 323 |
| 43 | 85000 | 14900 | 0.18 | 0.84 | 343 |

TABLE 3

|  | $\epsilon$ | $\epsilon\phi$ | $\phi$ | excitation max. (nm) |
| --- | --- | --- | --- | --- |
| 44 | 57000 | 8500 | 0.15 | 340 |
| 48 | 59000 | 3300 | 0.06 | 320 |

Example 42

Labeling of Antibody with Compound 14 and 39

Labeling of an TnI antibody was performed as described in von Lode P. et al., *Anal. Chem.*, 2003, 75, 3193-3201 by using a 90 fold excess of the compounds 14 and 39. The reaction was carried out overnight at RT. Labeled antibody was separated from the excess of the chelate on Superdex 200 HR 10/30 gel filtration column (GE healthcare) by using Tris-saline-azide (Tris 50 mM, NaCl 0.9%, pH 7.75) buffer as an eluent. The fractions containing the antibody were pooled and the europium concentration was measured against Eu standard material with Victor™ plate-fluorometer. The labelling degree of ~2.6 labels/antibody was obtained, The measured photo-physical properties excitation wavelengths ($\lambda_{exc}$), luminescence decay times ($\tau$), molar absorptivities ($\epsilon$), luminescence yields ($\epsilon\phi$) of the labelled cTnIs with the chelates 14 compared to the chelate 39 in 50 mM TRIS buffer (pH 7.75) in the Table 4. Dry measurements (14 (dry) and 39 (dry)) represents estimated luminescence yields based on the signal measurements after dry immunoassay done as described in the literature (von Lode P. et al., *Anal. Chem.*, 2003, 75, 3193-3201).

TABLE 4

| Labeled IgG with chelate | $\epsilon$ | $\epsilon\phi$ | $\phi$ | mean lifetime (ms) | excitation max. (nm) |
| --- | --- | --- | --- | --- | --- |
| 39 dry | 70000 | 9100 10200 | 0.13 | 0.90 | 323 |
| 14 dry | 77000 | 16100 14500 | 0.21 | 0.80 | 343 |

Example 43

Excitation Spectrum of Labeled Antibody

Figure 2:
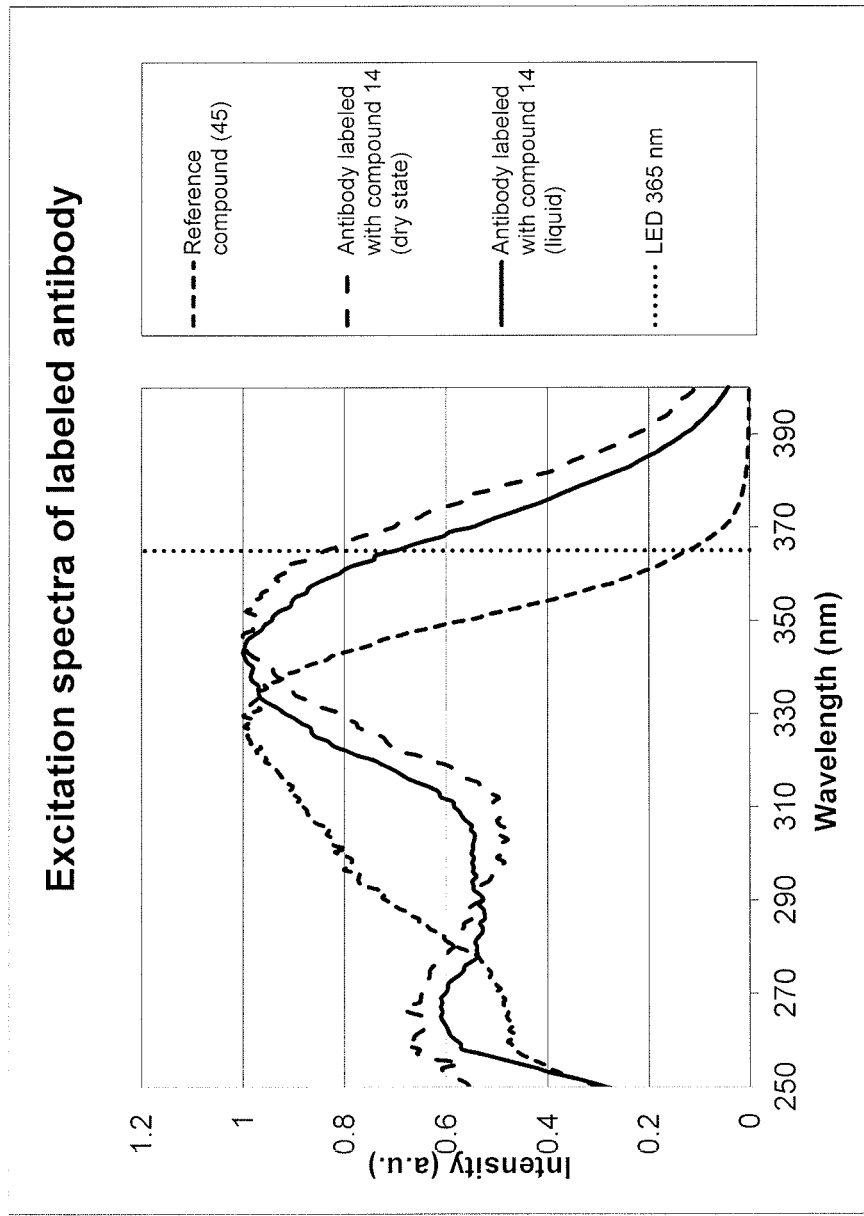
FIG. 2 shows the comparison of the excitation spectrum of a chelate according to an embodiment of the present disclosure to the excitation spectrum of reference compound (45).

The excitation spectrum of the purified tracer antibody labelled with compound 14 was measured both in liquid phase and in dry state. For comparison also an excitation spectrum of the reference compound 45 is presented in FIG. 2. (liquid phase measurement, dashed line). The excitation spectrum of the antibody labelled with compound 14 shows dear red-shift compared to the reference compound in the excitation maximum.

Example 44

Troponin I Immunoassay

The performance of the new chelate (14) was evaluated also in sandwich immunoassay for cardiac troponin I. As a reference compound a TnI antibody labelled with compound 45 (labelling degree 10 EuI/IgG) was used. 10 μl of diluted tracer antibody (5 ng/μl) and 20 μl of TnI standard solution were pipetted to a pre-coated assay well (single wells in 96 well plate format, wells coated with streptavidin and a biotinylated capture antibody against TnI, Innotrac Diagnostics). The reaction mixtures were incubated 20 min at 36° C. with shaking. The wells were washed 6 times and dried prior to measurement with Victor™ Plate-fluorometer using a 340 nm excitation wavelength. The results are summarized in Table 5. Both A and B standards were measured in 12 replicates and other standards C-F in 6 replicates. The results are presented in Table 5.

TABLE 5

| | cTnI std (ng/ml) | A 0 | B 0.022 | C 0.08 | D 0.75 | E 5.34 | F 41.6 |
|---|---|---|---|---|---|---|---|
| Antibody labeled with compound 14 | cps-blank | 213 | 600 | 2108 | 17187 | 122616 | 866665 |
| Reference antibody labeled with compound 45 | cps-blank | 183 | 267 | 906 | 7548 | 55086 | 427600 |
| Antibody labeled with compound 14 | cv % | 6.6 | 5.9 | 5.5 | 2.1 | 2.3 | 0.7 |
| Reference antibody labeled with compound 45 | cv % | 9.7 | 5.5 | 4.2 | 2.3 | 3.4 | 3.6 |

The results show that the chelate (14) provides the same signal levels with 1/10 amount of chelate/IgG when compared to the reference compound. In other words the compound according to present Disclosure provides an order of magnitude more luminescence signal per chelate than the state of the art reference compound. Noteworthy is that the excitation wavelength was 340 nm which was standard setting in the plate-fluorometer. If the excitation would have taken place at 365 nm the difference between the two chelates can be assumed even larger in favor of the new chelate. Noteworthy is also that the obtained CV%'s and background signals were excellent for the new chelate.

Example 45

Photo-Physical Properties of a Novel Chelate Conjugated to Taurine (Chelate 31)

The prepared isothiocyante activated chelate (30) was conjugated to taurine as described above in Example 38. The product was purified with semi-preparative reversed phase HPLC (RP-18 column). Rf(HPLC)=14.3 min. UV/VIS=349 nm. After the product fractions were evaporated the residues were dissolved in 50 mM TRS buffer.

The measured photo-physical properties excitation wavelengths ($\lambda_{exc}$), luminescence decay times ($\tau$), molar absorptivities ($\epsilon$), estimated luminescence yields ($\epsilon\Phi$) of the novel chelate (31) in 50 mM TRS buffer (pH 7.75) are in the Table 6.

TABLE 6

| Chelate | $\epsilon$ | $\epsilon\Phi$ | Mean lifetime (ms) | Excitation max. (nm) |
|---|---|---|---|---|
| 31 | 64,000 | 16,400 | 0.70 | 343 |

Example 46

Labelling of Antibody with Chelates 30

The TnI labeled antibodies were prepared as described in Example 42. The measured photo-physical properties excitation wavelengths ($\lambda_{exc}$), luminescence decay times ($\tau$), molar absorptivities ($\epsilon$), luminescence yields ($\epsilon\Phi$) of the labelled cTnIs with the chelate 30 in 50 mM TRIS buffer (pH 7.75) in Table 7. Dry measurements (30 (dry)) represent estimated luminescence yields based on the signal measurements after dry immunoassay done as described in the Example 44, The luminescence yield of labeled IgG (30) in dry is surprisingly high, further the obtained excitation max is also high,

TABLE 7

| Labeled IgG with chelate | $\epsilon$ | $\epsilon\Phi$ | mean lifetime (ms) | excitation max. (nm) |
|---|---|---|---|---|
| 30 | 78,000 | 11,400 | 0.69 | 344 |
| dry | | 20,700 | | |

Other embodiments will be apparent to those skilled in the art from consideration of the specification and practice of the present disclosure. It is intended that the specification and examples be considered as exemplary only, with a true scope and spirit of the invention being indicated by the following claims.

The invention claimed is:

1. A luminescent lanthanide chelate, wherein the luminescent lanthanide chelate has a structural formula selected from the group consisting of:

Formula (A-I)
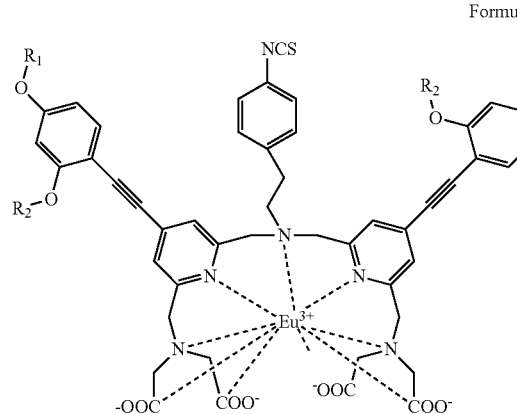
Formula (A-II)
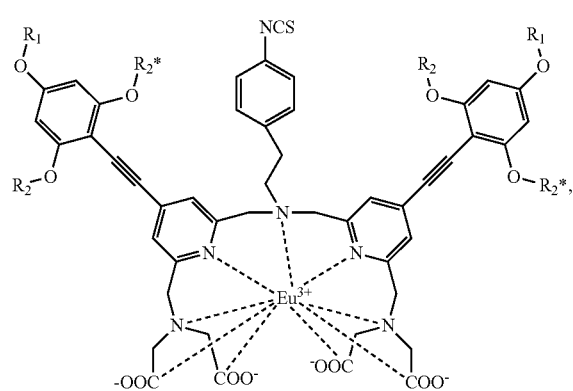
Formula (B-I)
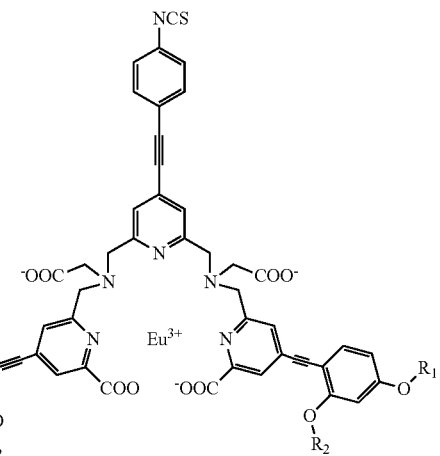
Formula (B-II)
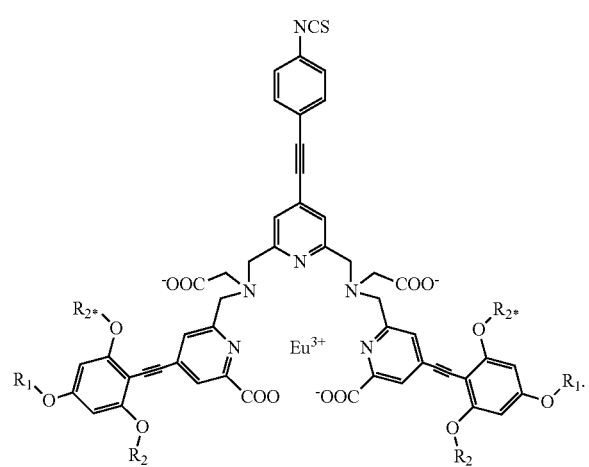
wherein the substituents $R_1$, $R_2$ and $R_{2*}$ are independently chosen from —$CH_2COOH$ and —$CH_2COO$—.
2. The luminescent lanthanide chelate according to claim 1, wherein the chelate further includes $Na^+$ as a counter ion.
3. A luminescent lanthanide chelate which is:
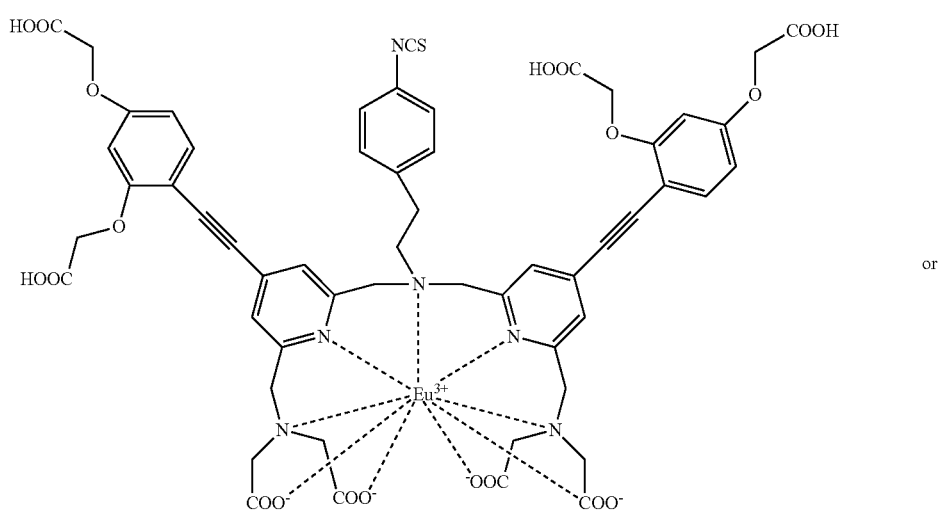
or

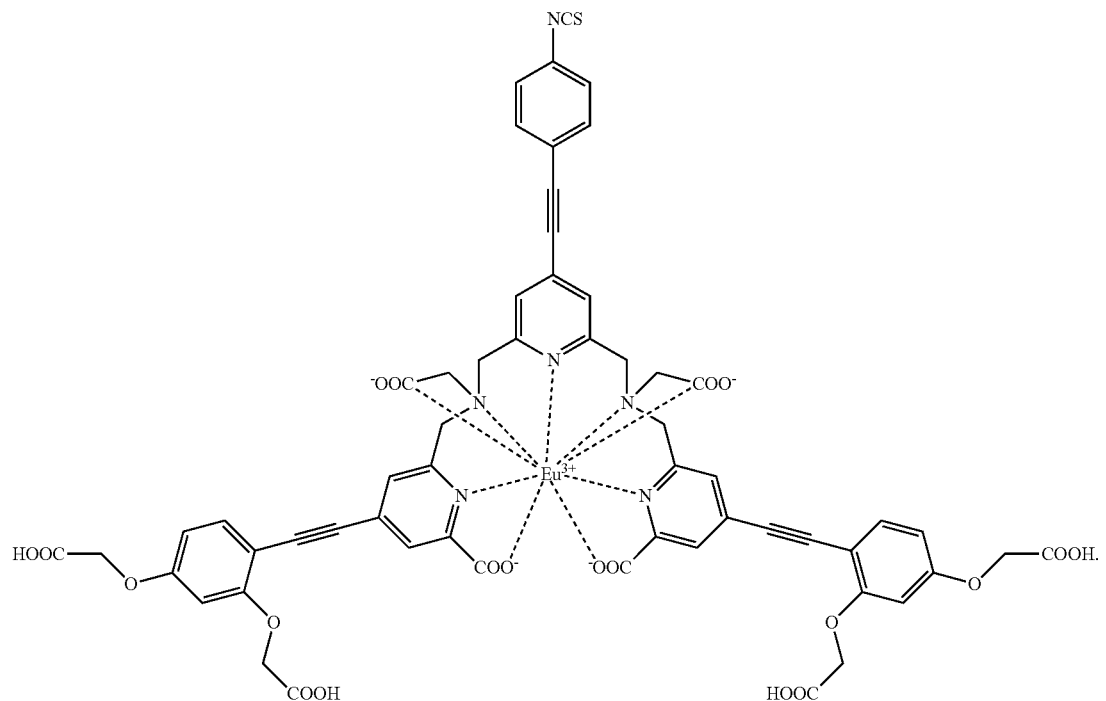
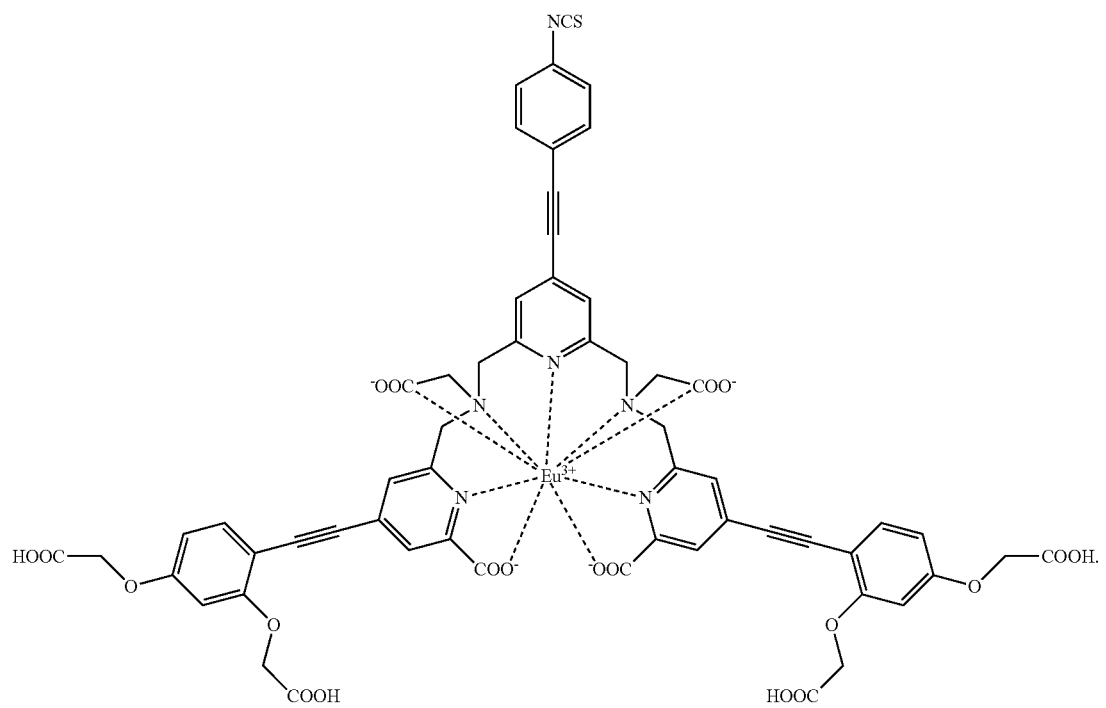

4. The luminescent lanthanide chelate of claim 3 which is

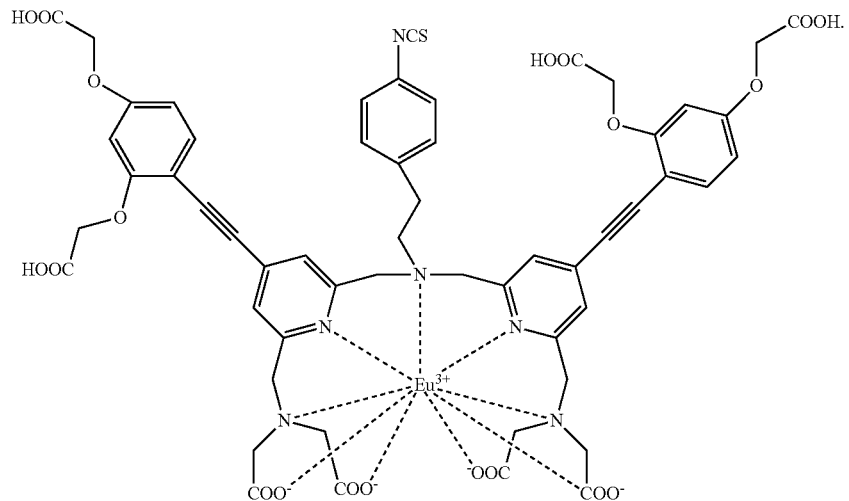

5. The luminescent lanthanide chelate of claim 3 which is

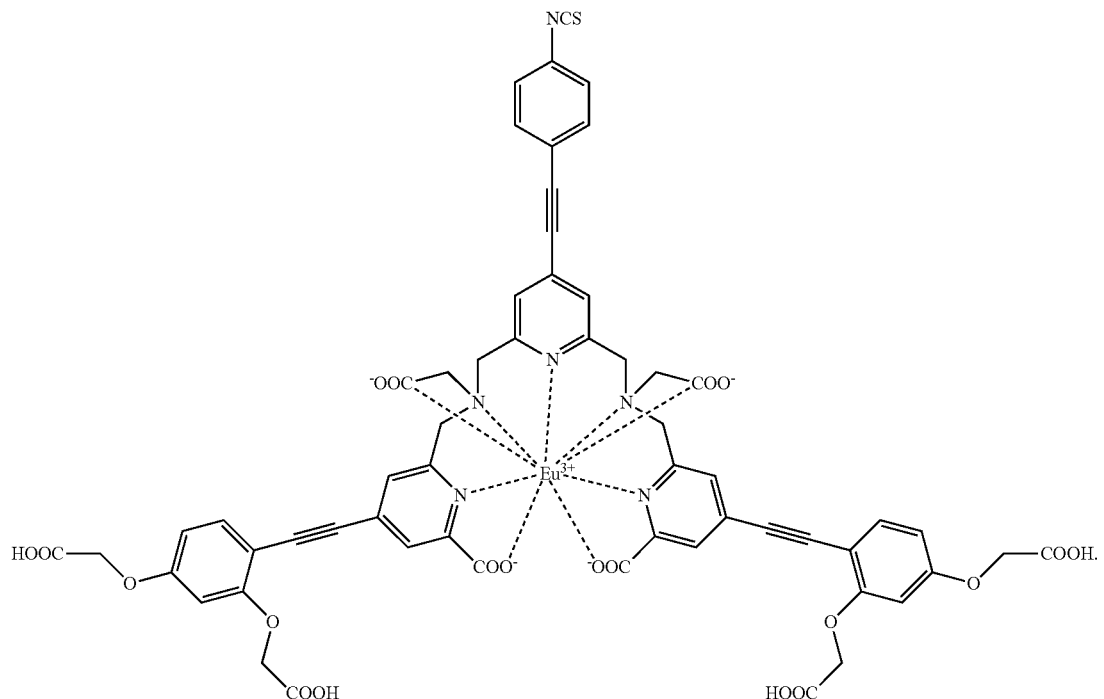

6. A detectable molecule comprising a biospecific binding reactant conjugated to a luminescent lanthanide as defined in claim 1.

7. The detectable molecule according to claim 6, wherein the biospecific binding reactant is an antibody, an antigen, a receptor ligand, a specific binding protein, a DNA probe, a RNA probe, an oligopeptide, an oligonucleotide, a modified oligonucleotide, a modified polynucleotide, a protein, an oligosaccharide, a polysaccharide, a phospholipid, a PNA, a steroid, a hapten, a drug, a receptor binding ligand, or lectine.

8. The detectable molecule according to claim 6, wherein the biospecific binding reactant is an antibody.

9. A method of carrying out a biospecific binding assay, comprising:
forming a biocomplex between an analyte and a biospecific binding reactant labeled with a luminescent lanthanide chelate according to claim 1;
exciting said biocomplex with radiation having an excitation wavelength, thereby forming an excited biocomplex; and
detecting emission radiation emitted from said excited biocomplex.

10. The method according to claim 9, wherein the specific bioaffinity based binding assay is selected from the group consisting of a heterogeneous immunoassay, a homogenous immunoassay, a DNA hybridization assay, a receptor binding assay, an immunocytochemical or an immunohistochemical assay.

11. A solid support material conjugated with a luminescent lanthanide chelate as defined in claim 1.

* * * * *

UNITED STATES PATENT AND TRADEMARK OFFICE
CERTIFICATE OF CORRECTION

PATENT NO. : 9,518,186 B2
APPLICATION NO. : 13/723505
DATED : December 13, 2016
INVENTOR(S) : Niko Meltola et al.

Page 1 of 5

It is certified that error appears in the above-identified patent and that said Letters Patent is hereby corrected as shown below:

In the Claims

In Claim 1, Column 32, Lines 1-20, Formula B-I:

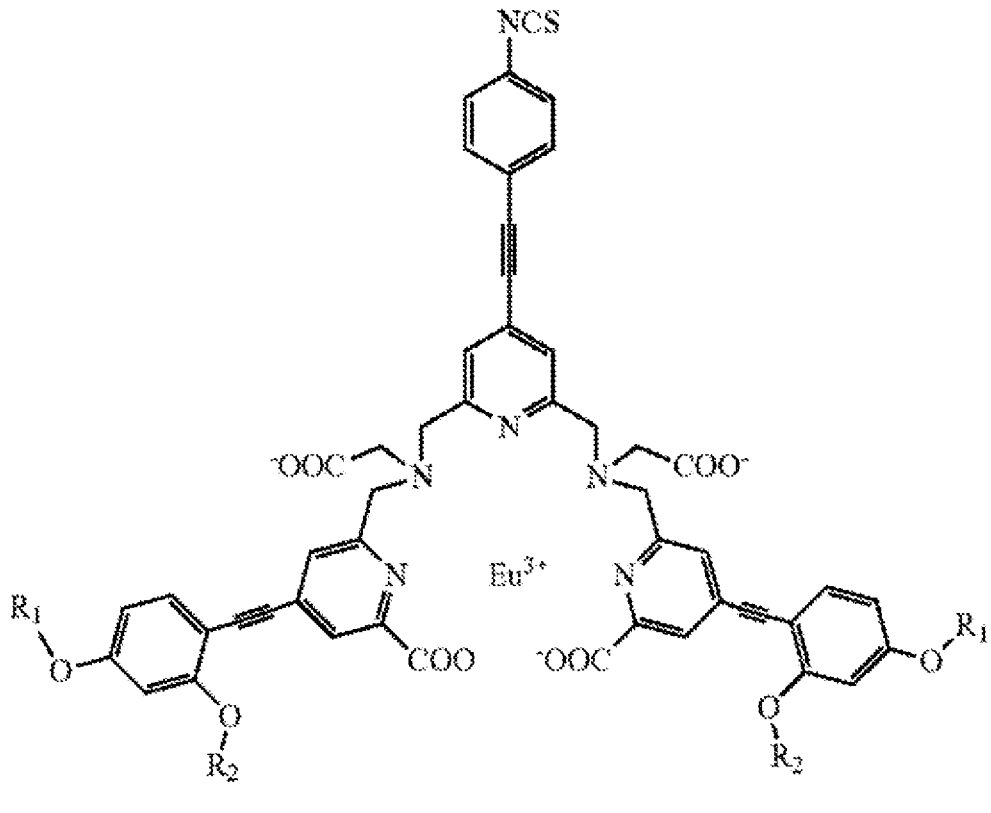

"                                                                              "

Should read:

Signed and Sealed this
Seventeenth Day of October, 2017

Joseph Matal
*Performing the Functions and Duties of the
Under Secretary of Commerce for Intellectual Property and
Director of the United States Patent and Trademark Office*

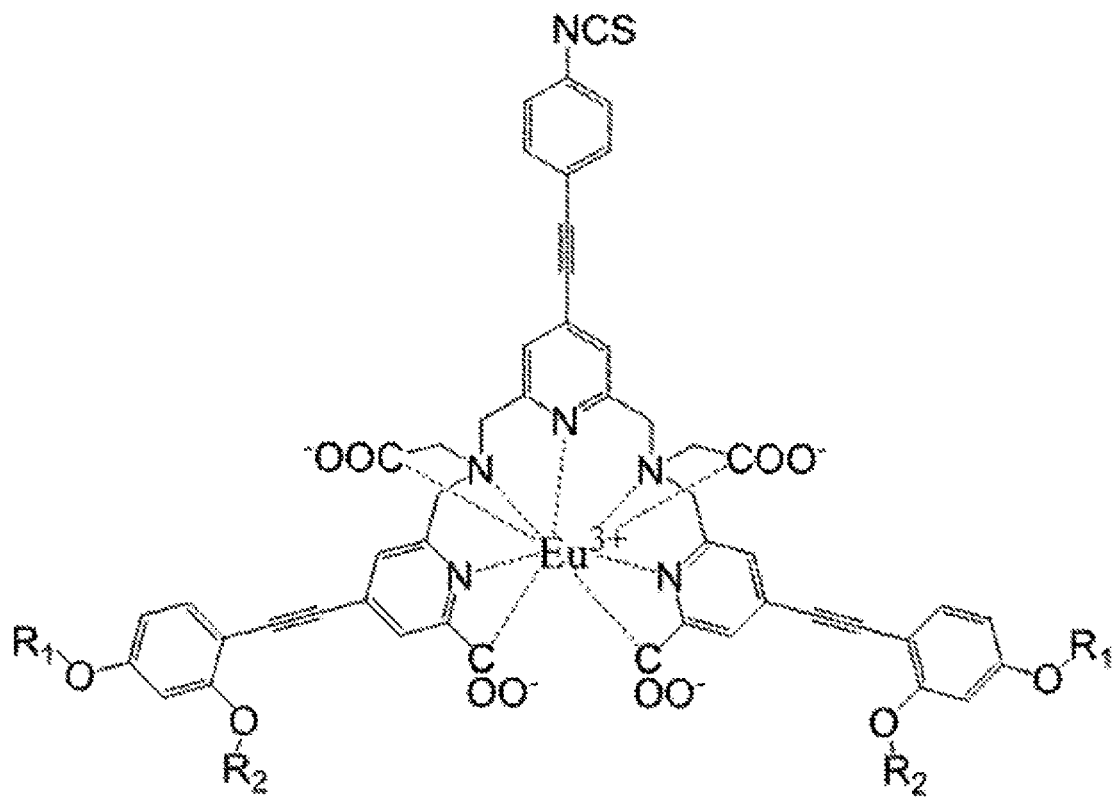
In Claim 1, Column 32, Lines 21-40, Formula B-II:

CERTIFICATE OF CORRECTION (continued)
U.S. Pat. No. 9,518,186 B2

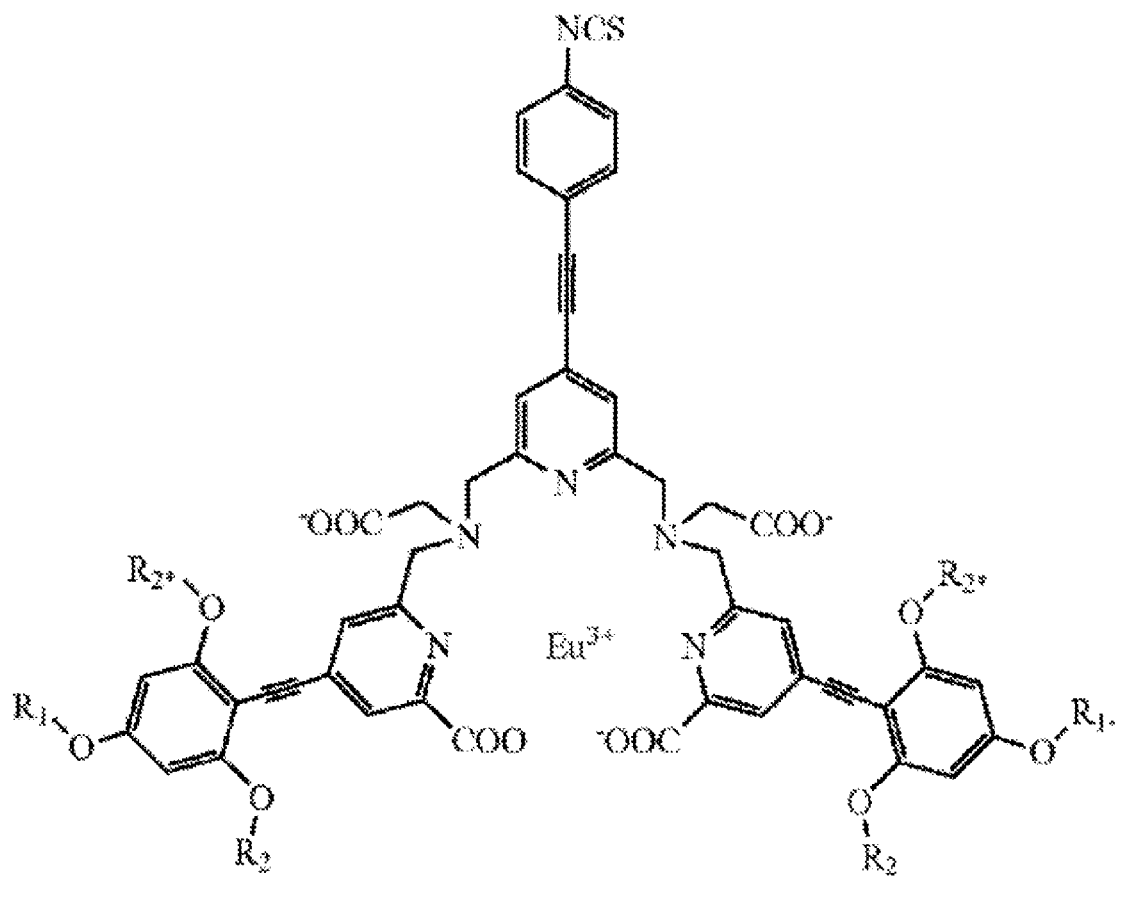

"

"

Should read:

CERTIFICATE OF CORRECTION (continued)
U.S. Pat. No. 9,518,186 B2

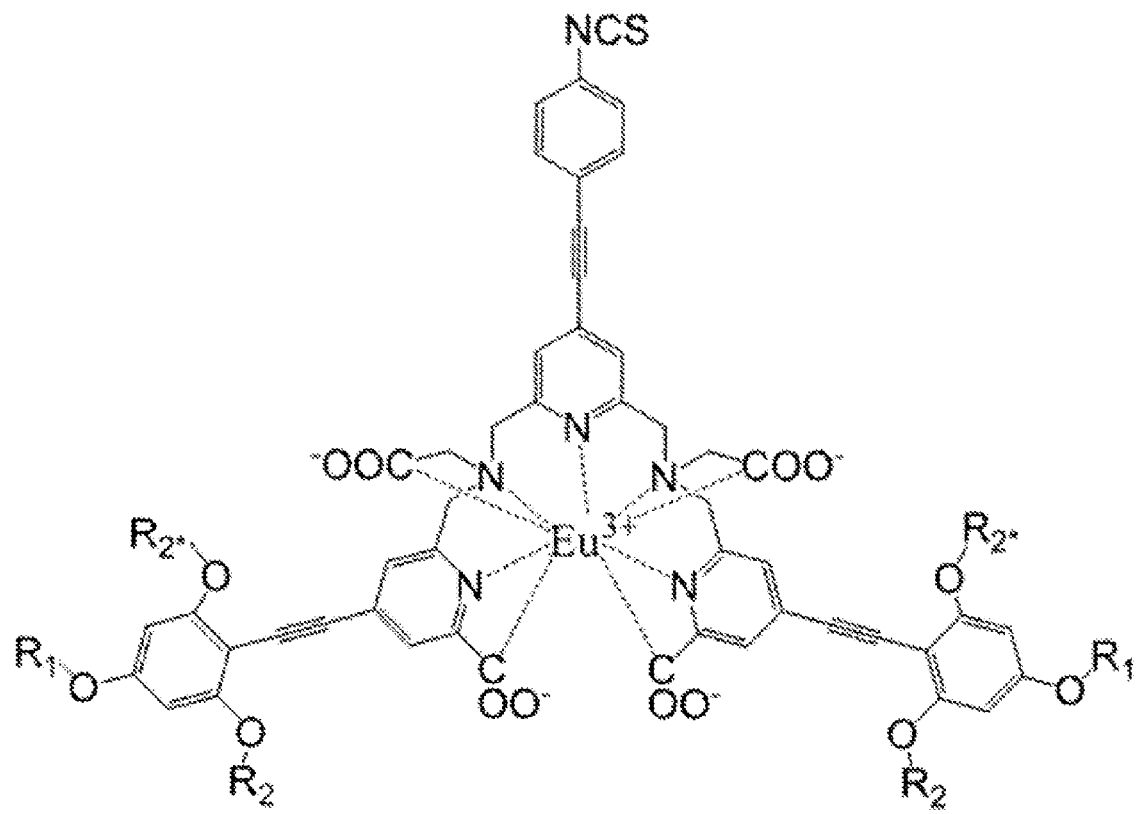

In Claim 3, Columns 33-34, second compound:

CERTIFICATE OF CORRECTION (continued)
U.S. Pat. No. 9,518,186 B2

Please delete the second occurrence of the compound:

"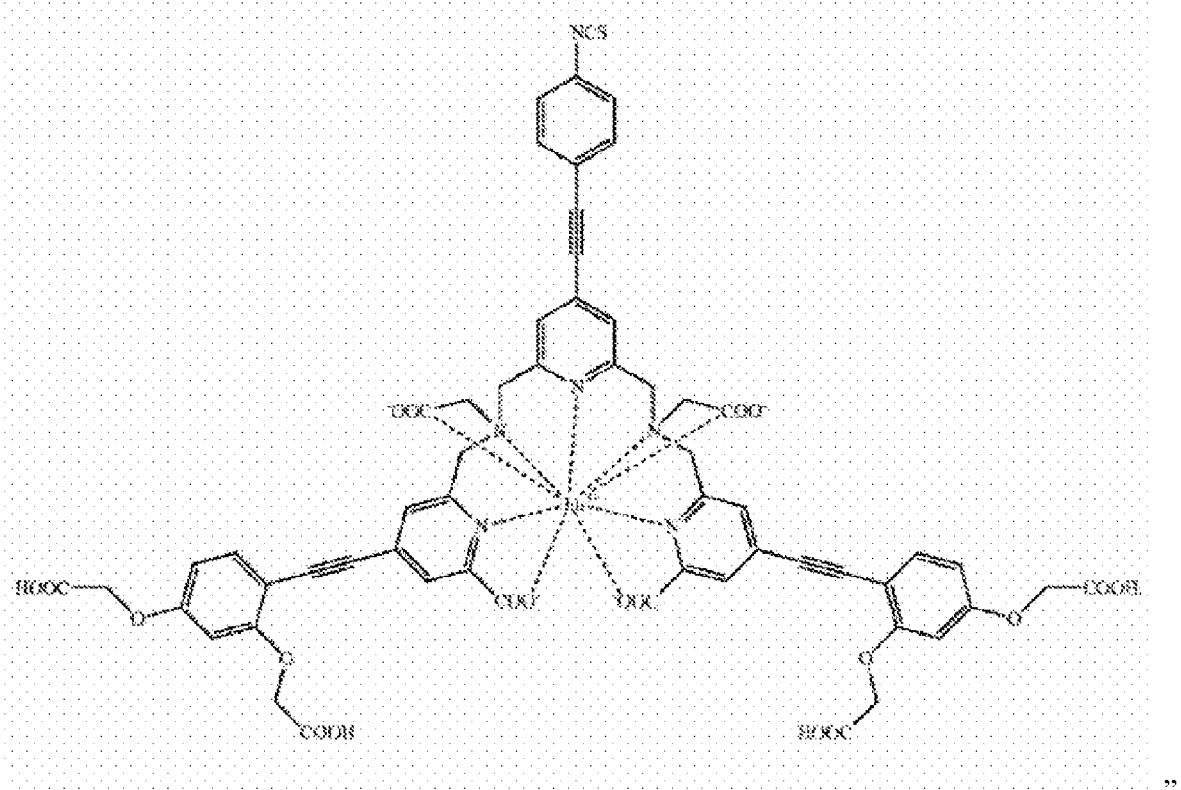"

Claim 6, Column 35, Lines 55-57:
"A detectable molecule comprising a biospecific binding reactant conjugated to a luminescent lanthanide as defined in claim 1." should read --A detectable molecule comprising a biospecific binding reactant conjugated to a luminescent lanthanide chelate as defined in claim 1.--